United States Patent [19]

Fowler et al.

[11] Patent Number: 6,022,725
[45] Date of Patent: *Feb. 8, 2000

[54] CLONING AND AMPLIFICATION OF THE β-GLUCOSIDASE GENE OF *TRICHODERMA REESEI*

[75] Inventors: Timothy Fowler, Belmont; Christopher C. Barnett, South San Francisco; Sharon Shoemaker, Fairfield, all of Calif.

[73] Assignee: Genencor International, Inc., Rochester, N.Y.

[*] Notice: This patent is subject to a terminal disclaimer.

[21] Appl. No.: 08/462,090

[22] Filed: Jun. 5, 1995

Related U.S. Application Data

[63] Continuation of application No. 07/625,140, Dec. 10, 1990, abandoned.

[51] Int. Cl.$^7$ .......................... C12N 15/55; C12N 15/80; C12Q 1/68

[52] U.S. Cl. ...................... 435/209; 435/6; 435/254.11; 435/254.3; 435/254.4; 435/254.5; 435/254.6; 435/320.1; 435/471; 435/484; 536/23.1; 536/23.2; 536/23.74; 536/24.3; 536/24.32; 536/24.33

[58] Field of Search ................................... 435/69.1, 203, 435/207, 6, 252.3, 254, 320.1, 172.3; 536/27, 23.2, 23.1, 23.74, 24.3

[56] References Cited

U.S. PATENT DOCUMENTS

| | | | |
|---|---|---|---|
| 4,275,163 | 6/1981 | Gallo | 435/209 |
| 4,472,504 | 9/1984 | Gallo | 435/209 |
| 4,745,062 | 5/1988 | Guerineau et al. | 435/209 |
| 4,885,252 | 12/1989 | Ingolia et al. | 435/252.33 |
| 4,935,349 | 6/1990 | McKnight et al. | 435/69.5 |

FOREIGN PATENT DOCUMENTS

| | | |
|---|---|---|
| 63-226 294 | 9/1988 | Japan . |
| 5 115 293 | 5/1993 | Japan . |
| WO92/06209 | 4/1992 | WIPO . |
| WO92/06210 | 4/1992 | WIPO . |

OTHER PUBLICATIONS

Meyer et al. Curr Gent 21:27–30 (1992) provided as BIOSIS Abstr. Acc# 93096373.
Barnett et al. Biotechnol. 9:562 (1991).
Gwynne et al. Biotechnol. 5:713 (1987).
Penttila et al. Gene 61:155 (1987).
Harkki et al. Biotechnol. 7:596 (1989).
Maniatis et al. Molecular Clonining CSH 1982 (pp. 226–227 & 432).
Shoemaker et al. Biotechnology vol. Oct., 1983 pp. 687–690.
Pouwels et al. Cloning Vectors Elsevier 1984,pp. V–A–L–1, V–A–ii–1.
Hofer et al. Biochem Biophys Acta 992(3):298–306, 1989 abstract only.
Maniatis et al. Molecular Cloning: a laboratory manual. CSH 1981 p. 228.
Penttila et al. Mol. Gen. Genet. 194(3):494–99 (1984) Abstract Only.
Young et al. PNAS vol. 80 pp. 1194–1198 (1983).
Kawamori, M., et al., "Preparation and application of *Trichoderma reesei* mutants with enhanced beta–glucosidase", *Agric. Biol. Chem.* 50(10), pp. 2477–2482 (1986).
Knowles, J., "Applications of the molecular biology of *Trichoderma reesei*", Proceedings of the EMBO–Alko Workshop on Molecular Biology of Filamentous Fungi, Helsinki 1989, ed. by H. Nevalainen and M. Penttila. pp. 113–118.
Strauss, J. and Kubicek, C.P. "Beta–glucosidase and cellulase formation by a *Trichoderma reesei* mutant defective in constitutive beta–glucosidase formation", *J. Gen. Microbiol.* 136, pp. 1321–1326 (1990).
Bause, E. and Legler, G., "Isolation and amino–acid sequence of a hexa deca peptide from the active site of beta–glucosidase A–3 from *Aspergillus wentii*", Hoppe–Seyler's Physiol. Chem. 355(4), pp. 438–442 (1974).
Staudenbauer, W.L., et al., "Nucleotide sequence of the *Clostridium thermocellum* bg1B gene encoding thermostable beta–glucosidase B: homology to fungal beta–glucosidase", Molecular General Genetics 217, pp. 70–76 (1989).
Bhikhabhai, P., et al., "Isolation of cellulolytic enzymes from *Trichoderma reesei*", J. Applied Biochemistry 6, pp. 336–345 (1984).
Miller Jr., R.C., et al., "Enzyme immobilization or purification using the cellulose–binding domains of the two bacterial cellulases", Protein Engrg. 3(4), p. 379 (1990).
Penttila, M.E., et al., "Cloning of *Aspergillus niger* genes in yeast. Expression of the gene coding Aspergillus beta–glucosidase", Molecular General Genetics, 194, pp. 494–499 (1984).
Raynal, A., et al., "Sequence and transcription of the beta–glucosidase gene of *Kluyvermyces fragilis* in *Saccharomyces cerevisiae*", Current Genetics 12, pp. 175–184 (1987).
Kalra, M.K., et al., "Partial purification, characterization, and regulation of cellulolytic enzymes from *Trichoderma longibrachiatum*", J. Applied Bacteriology 61, pp. 73–80 (1986).
Yelton, M.M., et al., "A cosmid for selecting genes by complementation in *Asperigillus nidulans*: selection of the developmentally regulated yA locus", *PNAS:USA* 82, pp. 834–838 (1985).

(List continued on next page.)

*Primary Examiner*—John L. LeGuyader
*Attorney, Agent, or Firm*—Susan Faris

[57] ABSTRACT

A process for expressing extracellular β-glucosidase in a filamentous fungus by expressing a fungal DNA sequence encoding enhanced, deleted or altered β-glucosidase in a recombinant host microorganism is disclosed. Recombinant fungal cellulase compositions containing enhanced, deleted or altered expression of β-glucosidase is also disclosed.

19 Claims, 10 Drawing Sheets

OTHER PUBLICATIONS

Wakarchuk, W.W., et al., "Structure and transcription analysis of the gene encoding a cellobiose from Agrobacterium sp. strain ATCC 21400", J. Bacteriology 170(1), pp. 301–307 (1988).

Penttila, M.E., et al., "Construction of brewer's yeast secreting fungal endo–beta–glucanase" Current Genetics 12, pp. 413–420 (1987).

Knowles, J., et al., "The cloning of fungal cellulase genes and their expression in yeast: cellobiohydrolase and beta–glucosidase gene expression in transformed *Saccharomyces cerevisiae*", FEBS Congress 16th Meeting, Part C, pp. 43–49 (1985).

Glick, B.R., et al., "Isolation, characterization, and manipulation of cellulase genes: cellobiohydrolase and beta–glucosidase genes cloning and expression; cellulase complex; a review", Biotechnol. Adv. 7(3), pp. 361–386.

Arnold, R., et al., Abstract, DD 263,571.

Gritzali, M. "Enzymes of the cellulase system of Trichoderma: an overview—cellulase complex characterization", Abstr. Pap. Am. Chem. Soc., 194 Meeting (1987).

Durand, H., et al., "Classical and molecular genetics applied to *Trichoderma reesi* for the selection of improved cellulolytic industrial strains—beta–glucosidase and cellulase actvity; beta–D–fructofuranosidase gene cloning and expression i *Trichoderma reesei*; cellulose degradation", FEMS Symp. vol. 43 (1988). See abstract No. 89–11621.

Barnett, C., et al., "Expression of *Trichoderma reesei* exo–cellobiohydrolase II genes in *Aspergillus awamori*: a heterologous expression system to study structure–function relationships—enzyme engineering applications", Abstr. Pap. Am. Chem. Soc., 195 Meeting (1988).

Knowles, J., et al., "The use of gene technology to investigate fungal cellulolytic enzymes—*Trichoderma reesei* cellulase complex gene cloning and expression in *Saccharomyces cerevisiae*", FEMS Symp. vol. 43 (1988).

Shoemaker, S.P., et al., "The cellulase system of *Trichoderma reesei*: Trichoderma strain improvement and expression of Trichoderma cellulase in yeast—in ethanol production", World Biotech. Rep. vol. 2, pp. 593–600 (1984).

Woldike, H. F., et al., WO Application 9117244. Published Nov. 14, 1991.

Ong, E., et al., "The cellulose binding domains of cellulase: tools for biotechnology–application in protein or fusion protein purification by affinity chromatography and in enzyme immobilization, a review", *Biotechnol.* 7(9), pp. 239–241 (1989). See abstract No. 89–12873.

Rickard, P.A.D., et al., "Kinetic properties and contribution to cellulose saccharification of a cloned Pseudomonas beta–glucosidase: enzyme cloning using plasmid pND71 and use of recombinant product in association with *Trichoderma reesei* cellulase", Aust. J. Biotechnol. 3(1), pp. 43–49 (1989).

```
TGGCCACAGA GGGAGAGTTC GCGCTACCGC TTGGTCGAGG AAATGATCGC CCACGGCCTC    60

AAATCGTAAA TCTCGGTGTG GGTAGGAGTG CAACGATGGG ATTTGGCCGC AATGCTGCCG   120

AGCCCGAGTG TTTCTGCAAC GTTATCCAGG AGATTTGCGC TTGCCCAAGA GGGAGTTGAC   180

GGGGAGAGTC CCAACTGGTT CCTTCAGTAA CGCCACCCTG GCAGACTATA TAACTTGTGG   240

ACAAGACTCT GCTTTGTTGA GTTCTTCCTA CCAGTCTTGA CCAAGACCAT TCTGTTGAGC   300

CCAATCAGAA ATG CGT TAC CGA ACA GCA GCT GCG CTG GCA CTT GCC ACT     349
           Met Arg Tyr Arg Thr Ala Ala Ala Leu Ala Leu Ala Thr
             1               5                  10
```

```
GGG CCC TTT GCT AGG GCA GAC AGT  CA  GTATAGCTGG TCCATACTGG         395
Gly Pro Phe Ala Arg Ala Asp Ser  His
 15                  20
```

```
GATGTGATAT GTATCCTGGA GACACCATGC TGACTCTTGA ATCAAGGTAG C TCA ACA   452
                                                         1 Ser Thr
```

```
TCG GGG GCC TCG GCT GAG GCA GTT GTA CCT CCT GCA GGG ACT CCA TGG    500
Ser Gly Ala Ser Ala Glu Ala Val Val Pro Pro Ala Gly Thr Pro Trp
 25           ↑ 30  ↑           35                      40

GGA ACC GCG TAC GAC AAG GCG AAG GCC GCA TTG GCA AAG CTC AAT CTC    548
Gly Thr Ala Tyr Asp Lys Ala Lys Ala Ala Leu Ala Lys Leu Asn Leu
                 45                  50                  55

CAA GAT AAG GTC GGC ATC GTG AGC GGT GTC GGC TGG AAC GGC GGT CCT    596
Gln Asp Lys Val Gly Ile Val Ser Gly Val Gly Trp Asn Gly Gly Pro
             60                  65                  70

TGC GTT GGA AAC ACA TCT CCG GCC TCC AAG ATC AGC TAT CCA TCG CTA    644
Cys Val Gly Asn Thr Ser Pro Ala Ser Lys Ile Ser Tyr Pro Ser Leu
         75                  80                  85

TGC CTT CAA GAC GGA CCC CTC GGT GTT CGA TAC TCG ACA GGC AGC ACA    692
Cys Leu Gln Asp Gly Pro Leu Gly Val Arg Tyr Ser Thr Gly Ser Thr
     90                  95                 100
                         *1
GCC TTT ACG CCG GGC GTT CAA GCG GCC TCG ACG TGG GAT GTC AAT TTG    740
Ala Phe Thr Pro Gly Val Gln Ala Ala Ser Thr Trp Asp Val Asn Leu
105                 110                 115                 120

ATC CGC GAA CGT GGA CAG TTC ATC GGT GAG GAG GTG AAG GCC TCG GGG    788
Ile Arg Glu Arg Gly Gln Phe Ile Gly Glu Glu Val Lys Ala Ser Gly
                 125                 130                 135

ATT CAT GTC ATA CTT GGT CCT GTG GCT GGG CCG CTG GGA AAG ACT CCG    836
Ile His Val Ile Leu Gly Pro Val Ala Gly Pro Leu Gly Lys Thr Pro
             140                 145                 150
```

*FIG._1A*

```
CAG GGC GGT CGC AAC TGG GAG GGC TTC GGT GTC GAT CCA TAT CTC ACG      884
Gln Gly Gly Arg Asn Trp Glu Gly Phe Gly Val Asp Pro Tyr Leu Thr
        155             160             165

GGC ATT GCC ATG GGT CAA ACC ATC AAC GGC ATC CAG TCG GTA GGC GTG      932
Gly Ile Ala Met Gly Gln Thr Ile Asn Gly Ile Gln Ser Val Gly Val
    170             175             180

CAG GCG ACA GCG AAG CAC TAT ATC CTC AAC GAG CAG GAG CTC AAT CGA      980
Gln Ala Thr Ala Lys His Tyr Ile Leu Asn Glu Gln Glu Leu Asn Arg
185             190             195             200

GAA ACC ATT TCG AGC AAC CCA GAT GAC CGA ACT CTC CAT GAG CTG TAT     1028
Glu Thr Ile Ser Ser Asn Pro Asp Asp Arg Thr Leu His Glu Leu Tyr
            205             210             215

ACT TGG CCA TTT GCC GAC GCG GTT CAG GCC AAT GTC GCT TCT GTC ATG     1076
Thr Trp Pro Phe Ala Asp Ala Val Gln Ala Asn Val Ala Ser Val Met
        220             225             230

TGC TCG TAC AAC AAG GTC AAT ACC ACC TGG GCC TGC GAG GAT CAG TAC     1124
Cys Ser Tyr Asn Lys Val Asn Thr Thr Trp Ala Cys Glu Asp Gln Tyr
        235             240             245

ACG CTG CAG ACT GTG CTG AAA GAC CAG CTG GGG TTC CCA GGC TAT GTC     1172
Thr Leu Gln Thr Val Leu Lys Asp Gln Leu Gly Phe Pro Gly Tyr Val
    250             255             260
                                *2
ATG ACG GAC TGG AAC GCA CAG CAC ACG ACT GTC CAA AGC GCG AAT TCT     1220
Met Thr Asp Trp Asn Ala Gln His Thr Thr Val Gln Ser Ala Asn Ser
265             270             275             280

GGG CTT GAC ATG TCA ATG CCT GGC ACA GAC TTC AAC GGT AAC AAT CGG     1268
Gly Leu Asp Met Ser Met Pro Gly Thr Asp Phe Asn Gly Asn Asn Arg
                285             290             295

CTC TGG GGT CCA GCT CTC ACC AAT GCG GTA AAT AGC AAT CAG GTC CCC     1316
Leu Trp Gly Pro Ala Leu Thr Asn Ala Val Asn Ser Asn Gln Val Pro
        300             305             310

ACG AGC AGA GTC GAC GAT ATG GTG ACT CGT ATC CTC GCC GCA TGG TAC     1364
Thr Ser Arg Val Asp Asp Met Val Thr Arg Ile Leu Ala Ala Trp Tyr
        315             320             325

TTG ACA GGC CAG GAC CAG GCA GGC TAT CCG TCG TTC AAC ATC AGC AGA     1412
Leu Thr Gly Gln Asp Gln Ala Gly Tyr Pro Ser Phe Asn Ile Ser Arg
    330             335             340

AAT GTT CAA GGA AAC CAC AAG ACC AAT GTC AGG GCA ATT GCC AGG GAC     1460
Asn Val Gln Gly Asn His Lys Thr Asn Val Arg Ala Ile Ala Arg Asp
345             350             355             360

GGC ATC GTT CTG CTC AAG AAT GAC GCC AAC ATC CTG CCG CTC AAG AAG     1508
Gly Ile Val Leu Leu Lys Asn Asp Ala Asn Ile Leu Pro Leu Lys Lys
            365             370             375
```

| | | | | | | | | | | | | | | | | |
|---|---|---|---|---|---|---|---|---|---|---|---|---|---|---|---|---|
| CCC | GCT | AGC | ATT | GCC | GTC | GTT | GGA | TCT | GCC | GCA | ATC | ATT | GGT | AAC | CAC | 1556 |
| Pro | Ala | Ser | Ile | Ala | Val | Val | Gly | Ser | Ala | Ala | Ile | Ile | Gly | Asn | His | |
| | | | 380 | | | | | 385 | | | | | 390 | | | |

| | | | | | | | | | | | | | | | | |
|---|---|---|---|---|---|---|---|---|---|---|---|---|---|---|---|---|
| GCC | AGA | AAC | TCG | CCC | TCG | TGC | AAC | GAC | AAA | GGC | TGC | GAC | GAC | GGG | GCC | 1604 |
| Ala | Arg | Asn | Ser | Pro | Ser | Cys | Asn | Asp | Lys | Gly | Cys | Asp | Asp | Gly | Ala | |
| | | 395 | | | | | 400 | | | | | 405 | | | | |

| | | | | | | | | | | | | | | | | |
|---|---|---|---|---|---|---|---|---|---|---|---|---|---|---|---|---|
| TTG | GGC | ATG | GGT | TGG | GGT | TCC | GGC | GCC | GTC | AAC | TAT | CCG | TAC | TTC | GTC | 1652 |
| Leu | Gly | Met | Gly | Trp | Gly | Ser | Gly | Ala | Val | Asn | Tyr | Pro | Tyr | Phe | Val | |
| | | 410 | | | | 415 | | | | | 420 | | | | | |

| | | | | | | | | | | | | | | | | |
|---|---|---|---|---|---|---|---|---|---|---|---|---|---|---|---|---|
| GCG | CCC | TAC | GAT | GCC | ATC | AAT | ACC | AGA | GCG | TCT | TCG | CAG | GGC | ACC | CAG | 1700 |
| Ala | Pro | Tyr | Asp | Ala | Ile | Asn | Thr | Arg | Ala | Ser | Ser | Gln | Gly | Thr | Gln | |
| 425 | | | | 430 | | | | | 435 | | | | | | 440 | |

| | | | | | | | | | | | | | | | | |
|---|---|---|---|---|---|---|---|---|---|---|---|---|---|---|---|---|
| GTT | ACC | TTG | AGC | AAC | ACC | GAC | AAC | ACG | TCC | TCA | GGC | GCA | TCT | GCA | GCA | 1748 |
| Val | Thr | Leu | Ser | Asn | Thr | Asp | Asn | Thr | Ser | Ser | Gly | Ala | Ser | Ala | Ala | |
| | | | | 445 | | | | | 450 | | | | | 455 | | |
| | | | | | | | | | *4 | | | | | | | |

| | | | | | | | | | | | | | | | | |
|---|---|---|---|---|---|---|---|---|---|---|---|---|---|---|---|---|
| AGA | GGA | AAG | GAC | GTC | GCC | ATC | GTC | TTC | ATC | ACC | GCC | GAC | TCG | GGT | GAA | 1796 |
| Arg | Gly | Lys | Asp | Val | Ala | Ile | Val | Phe | Ile | Thr | Ala | Asp | Ser | Gly | Glu | |
| | | | | 460 | | | | | 465 | | | | | 470 | | |

| | | | | | | | | | | | | | | | | |
|---|---|---|---|---|---|---|---|---|---|---|---|---|---|---|---|---|
| GGC | TAC | ATC | ACC | GTG | GAG | GGC | AAC | GCG | GGC | GAT | CGC | AAC | AAC | CTG | GAT | 1844 |
| Gly | Tyr | Ile | Thr | Val | Glu | Gly | Asn | Ala | Gly | Asp | Arg | Asn | Asn | Leu | Asp | |
| | | | 475 | | | | | 480 | | | | | 485 | | | |

| | | | | | | | | | | | | | | | | |
|---|---|---|---|---|---|---|---|---|---|---|---|---|---|---|---|---|
| CCG | TGG | CAC | AAC | GGC | AAT | GCC | CTG | GTC | CAG | GCG | GTG | GCC | GGT | GCC | AAC | 1892 |
| Pro | Trp | His | Asn | Gly | Asn | Ala | Leu | Val | Gln | Ala | Val | Ala | Gly | Ala | Asn | |
| | | | 490 | | | | | 495 | | | | | 500 | | | |

| | | | | | | | | | | | | | | | | |
|---|---|---|---|---|---|---|---|---|---|---|---|---|---|---|---|---|
| AGC | AAC | GTC | ATT | GTT | GTT | GTC | CAC | TCC | GTT | GGC | GCC | ATC | ATT | CTG | GAG | 1940 |
| Ser | Asn | Val | Ile | Val | Val | Val | His | Ser | Val | Gly | Ala | Ile | Ile | Leu | Glu | |
| 505 | | | | | 510 | | | | | 515 | | | | | 520 | |

| | | | | | | | | | | | | | | | | |
|---|---|---|---|---|---|---|---|---|---|---|---|---|---|---|---|---|
| CAG | ATT | CTT | GCT | CTT | CCG | CAG | GTC | AAG | GCC | GTT | GTC | TGG | GCG | GGT | CTT | 1988 |
| Gln | Ile | Leu | Ala | Leu | Pro | Gln | Val | Lys | Ala | Val | Val | Trp | Ala | Gly | Leu | |
| | | | | 525 | | | | | 530 | | | | | 535 | | |

| | | | | | | | | | | | | | | | | |
|---|---|---|---|---|---|---|---|---|---|---|---|---|---|---|---|---|
| CCT | TCT | CAG | GAG | AGC | GGC | AAT | GCG | CTC | GTC | GAC | GTG | CTG | TGG | GGA | GAT | 2036 |
| Pro | Ser | Gln | Glu | Ser | Gly | Asn | Ala | Leu | Val | Asp | Val | Leu | Trp | Gly | Asp | |
| | | | 540 | | | | | 545 | | | | | 550 | | | |

| | | | | | | | | | | | | | | | | |
|---|---|---|---|---|---|---|---|---|---|---|---|---|---|---|---|---|
| GTC | AGC | CCT | TCT | GGC | AAG | CTG | GTG | TAC | ACC | ATT | GCG | AAG | AGC | CCC | AAT | 2084 |
| Val | Ser | Pro | Ser | Gly | Lys | Leu | Val | Tyr | Thr | Ile | Ala | Lys | Ser | Pro | Asn | |
| | | 555 | | | | | 560 | | | | | 565 | | | | |

| | | | | | | | | | | | | | | | | |
|---|---|---|---|---|---|---|---|---|---|---|---|---|---|---|---|---|
| GAC | TAT | AAC | ACT | CGC | ATC | GTT | TCC | GGC | GGC | AGT | GAC | AGC | TTC | AGC | GAG | 2132 |
| Asp | Tyr | Asn | Thr | Arg | Ile | Val | Ser | Gly | Gly | Ser | Asp | Ser | Phe | Ser | Glu | |
| | | 570 | | | | | 575 | | | | | 580 | | | | |

| | | | | | | | | | | | | | | | | |
|---|---|---|---|---|---|---|---|---|---|---|---|---|---|---|---|---|
| GGA | CTG | TTC | ATC | GAC | TAT | AAG | CAC | TTC | GAC | GAC | GCC | AAT | ATC | ACG | CCG | 2180 |
| Gly | Leu | Phe | Ile | Asp | Tyr | Lys | His | Phe | Asp | Asp | Ala | Asn | Ile | Thr | Pro | |
| 585 | | | | | 590 | | | | | 595 | | | | | 600 | |

FIG._1C

```
CGG TAC GAG TTC GGC TAT GGA CTG   T GTAAGTTTGC TAACCTGAAC            2225
Arg Tyr Glu Phe Gly Tyr Gly Leu   6
                605

AATCTATTAG ACAGGTTGAC TGACGGATGA CTGTGGAATG ATAG   CT TAC ACC AAG    2280
                                                     Ser Tyr Thr Lys
                                                              610
              *5
TTC AAC TAC TCA CGC CTC TCC GTC TTG TCG ACC GCC AAG TCT GGT CCT      2328
Phe Asn Tyr Ser Arg Leu Ser Val Leu Ser Thr Ala Lys Ser Gly Pro
            615                 620                 625

GCG ACT GGG GCC GTT GTG CCG GGA GGC CCG AGT GAT CTG TTC CAG AAT      2376
Ala Thr Gly Ala Val Val Pro Gly Gly Pro Ser Asp Leu Phe Gln Asn
        630                 635                 640
                             *6
GTC GCG ACA GTC ACC GTT GAC ATC GCA AAC TCT GGC CAA GTG ACT GGT      2424
Val Ala Thr Val Thr Val Asp Ile Ala Asn Ser Gly Gln Val Thr Gly
645                 650                 655                 660

GCC GAG GTA GCC CAG CTG TAC ATC ACC TAC CCA TCT TCA GCA CCC AGG      2472
Ala Glu Val Ala Gln Leu Tyr Ile Thr Tyr Pro Ser Ser Ala Pro Arg
                665                 670                 675

ACC CCT CCG AAG CAG CTG CGA GGC TTT GCC AAG CTG AAC CTC ACG CCT      2520
Thr Pro Pro Lys Gln Leu Arg Gly Phe Ala Lys Leu Asn Leu Thr Pro
            680                 685                 690

GGT CAG AGC GGA ACA GCA ACG TTC AAC ATC CGA CGA CGA GAT CTC AGC      2568
Gly Gln Ser Gly Thr Ala Thr Phe Asn Ile Arg Arg Arg Asp Leu Ser
        695                 700                 705

TAC TGG GAC ACG GCT TCG CAG AAA TGG GTG GTG CCG TCG GGG TCG TTT      2616
Tyr Trp Asp Thr Ala Ser Gln Lys Trp Val Val Pro Ser Gly Ser Phe
    710                 715                 720
*7
GGC ATC AGC GTG GGA GCG AGC AGC CGG GAT ATC AGG CTG ACG AGC ACT      2664
Gly Ile Ser Val Gly Ala Ser Ser Arg Asp Ile Arg Leu Thr Ser Thr
725                 730                 735                 740

CTG TCG GTA GCG TAG CGCGAGG AGGGTGAAGG CGGTTGACCT GTGACTGTGA         2716
Leu Ser Val Ala AN*
                745

GTGAGGACCG AAGGTGGGAT GGCGTGAATA CTGCAGGAAT ACAATCTTCA GGATAGGCAT    2776

CAGAGCAGTA ACATGAATGA TGAAGACGGC CGAAGCAGAA GTGAATTGAG GAGGTAGTGA    2836

TGATGAAATG TGAGGGAAGA GAGATGTTCA ATCACCTTGT TCGAGGGAAG CTGCAAATTG    2896

GGCCTCACGT CATCTCGCAG AGAGAAGGAA CTCTTGCAGC AGGAGTTCTG CTCACTGAGA    2956

AGAAGGCCCG GGTTAGCGTC GCGCCTCTTC CGCGACATCC TCCGCTCCGG CACTGTGCTG    3016

TCAAACTGGC ACCAACA                                                   3033
```

FIG._1D

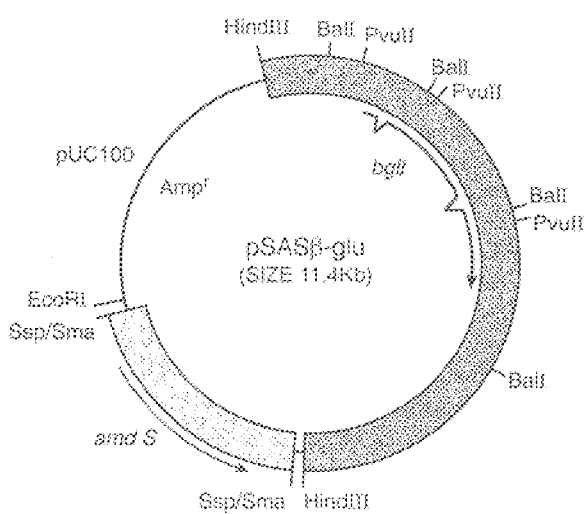
FIG._2
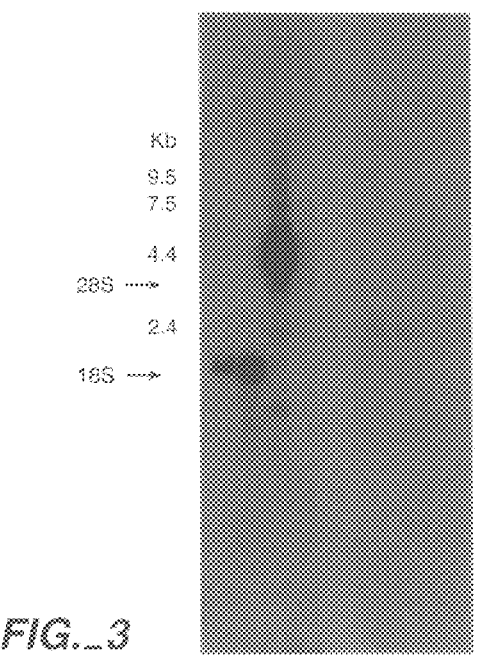
FIG._3

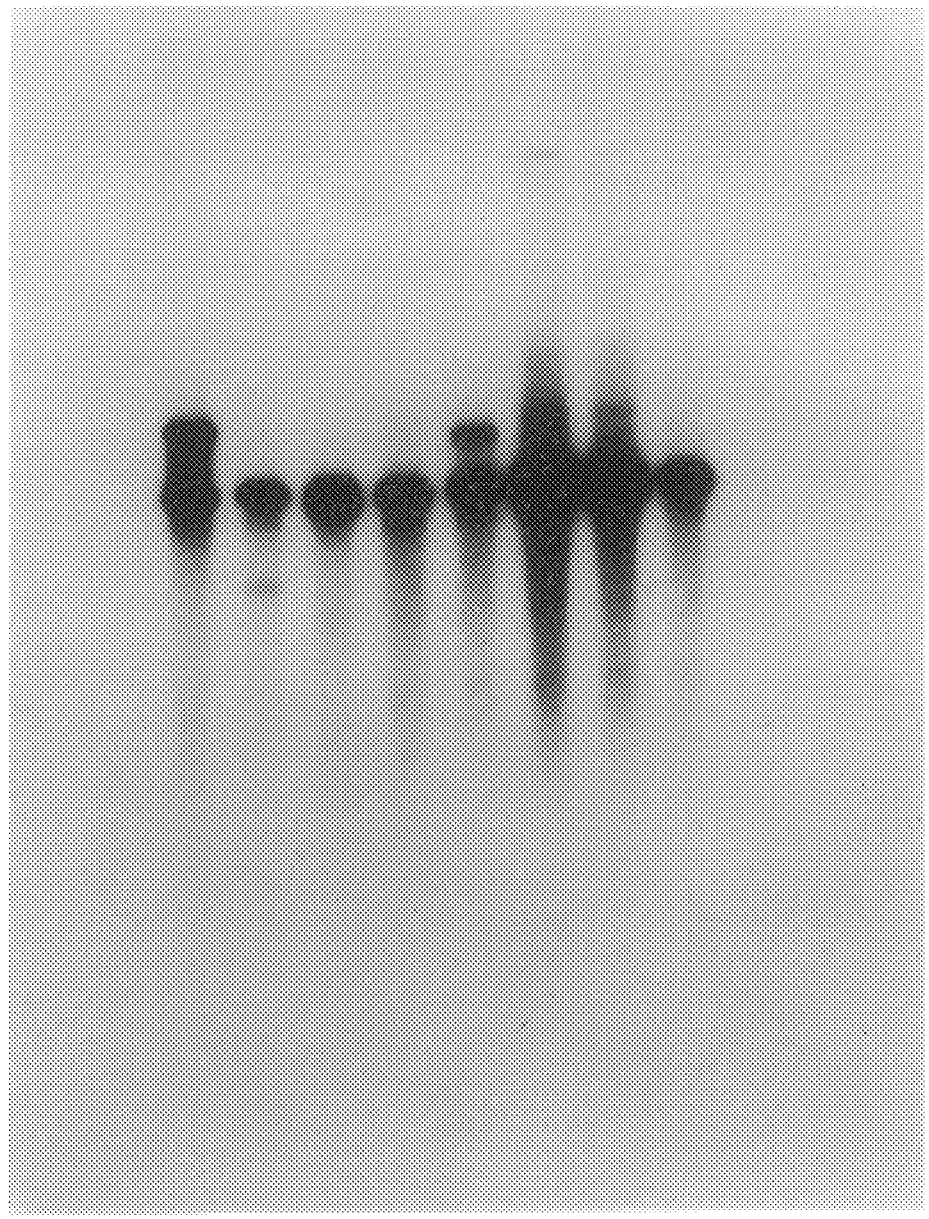
FIG._4

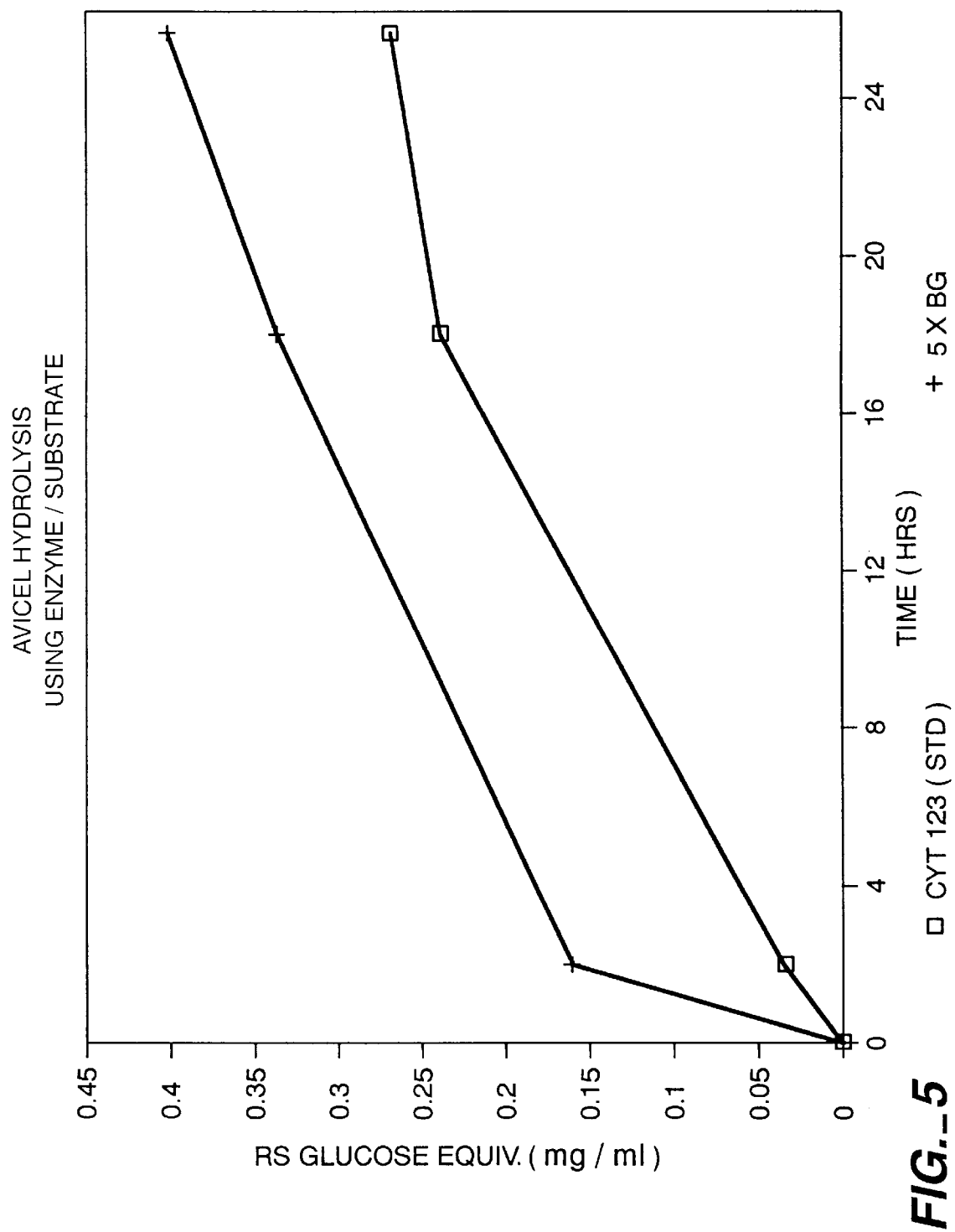
FIG._5

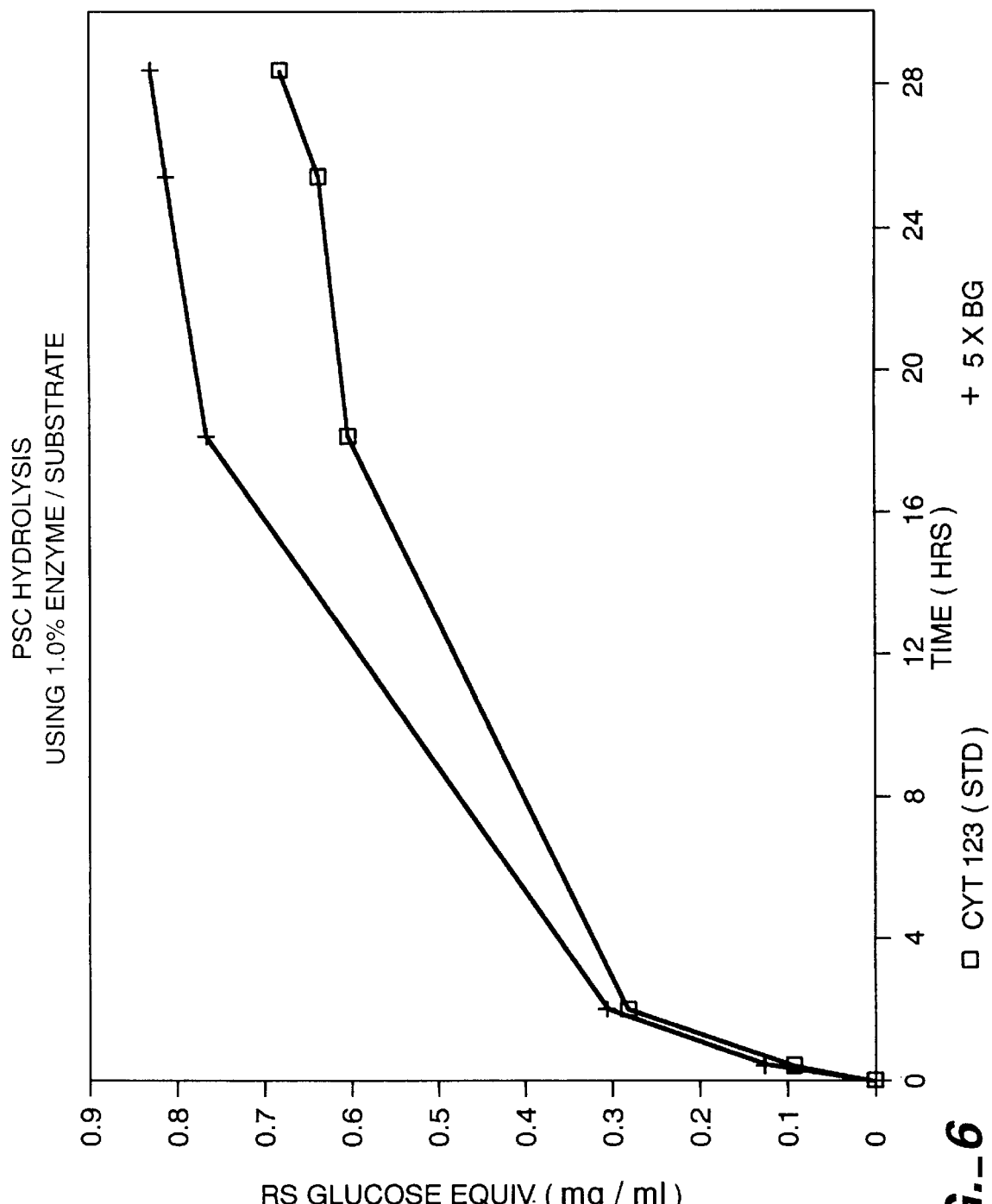
FIG._6

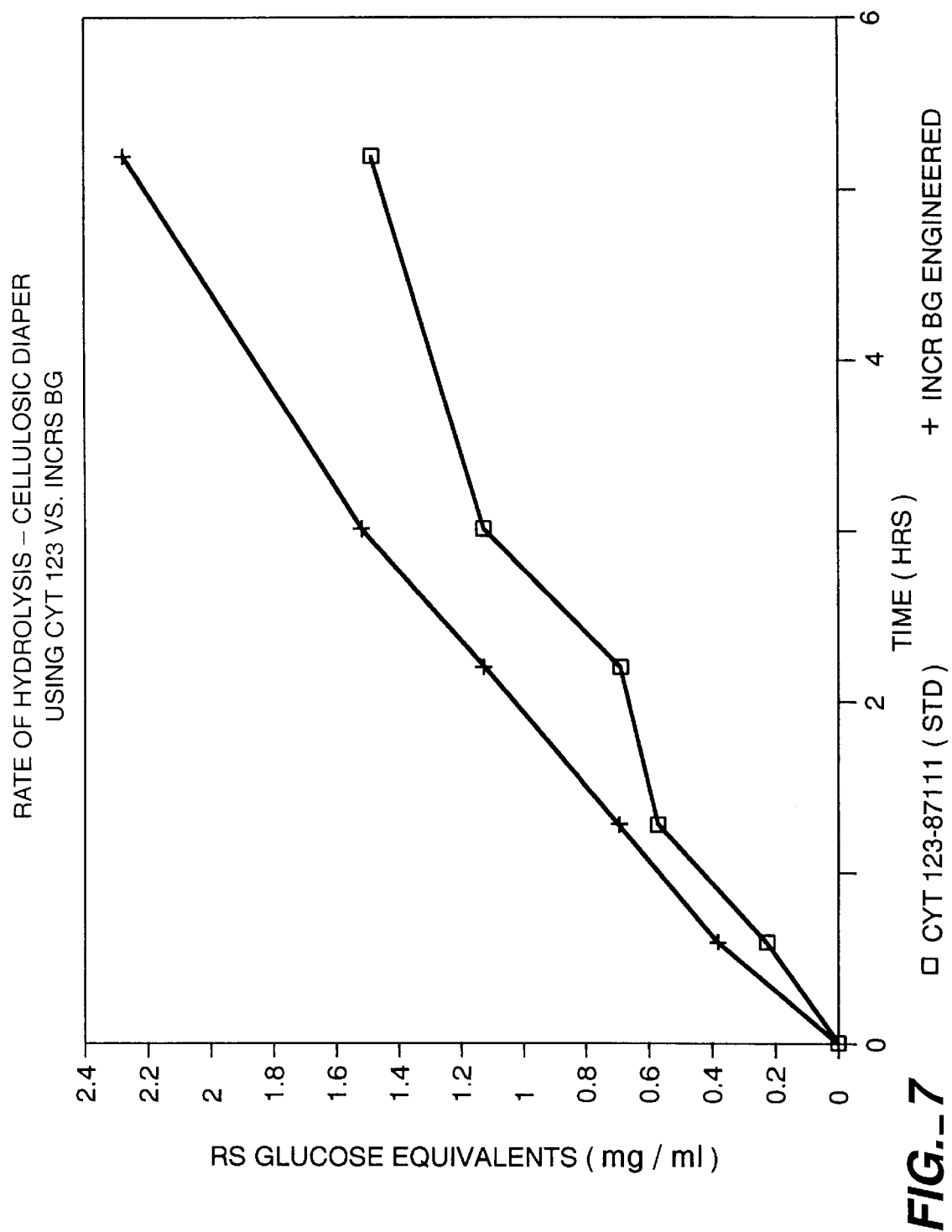

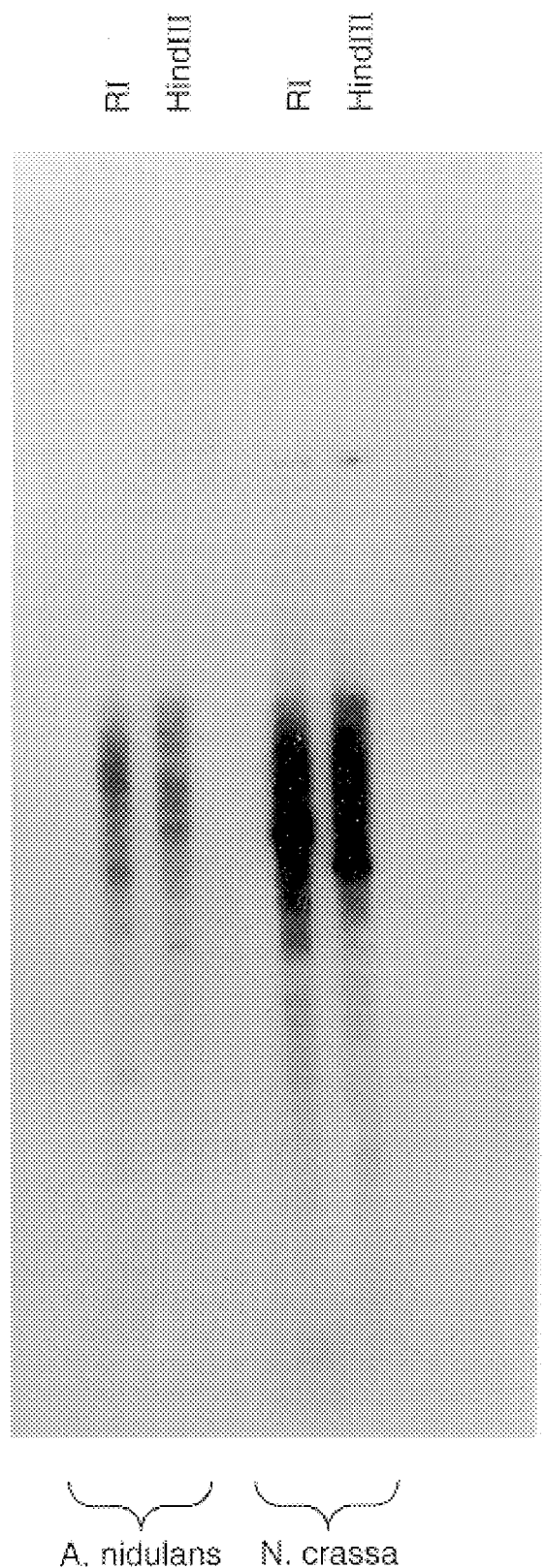
FIG._8

CLONING AND AMPLIFICATION OF THE β-GLUCOSIDASE GENE OF *TRICHODERMA REESEI*

This is a Continuation of application Ser. No. 07/625,140 filed Dec. 10, 1990, now abandoned.

BACKGROUND OF THE INVENTION

1. Field of the Invention

The present invention relates to a cellulase preparation and compositions having increased cellulolytic capacity which is useful for increased cellulosic degradation. The invention further relates to a nucleotide sequence of the bgl1 gene encoding extracellular β-glucosidase from *Trichoderma reesei*, a plasmid vector containing the gene encoding extracellular β-glucosidase and transformant strains with increased copy numbers of the β-glucosidase (bgl1) gene introduced into the genome. More particularly, the present invention relates to a *Trichoderma reesei* strain that has increased levels of expression of the bgl1 gene resulting in enhanced β-glucosidase protein levels that can be used in conjunction with other compositions to produce a cellulase product having increased cellulolytic capacity.

2. State of the Art

Cellulases are known in the art as enzymes that hydrolyze cellulose (β-1,4-glucan linkages), thereby resulting in the formation of glucose, cellobiose, cellooligosaccharides, and the like. As noted in "Methods in Enzymology", 160, 25, pages 234 et seq. (1988) and elsewhere, a cellulase system produced by a given microorganism is comprised of several different enzyme components including those identified as exocellobiohydrolases (EC 3.2.1.91) ("CBH"), endoglucanases (EC 3.2.1.4) ("EG"), β-glucosidases (EC 3.2.1.21) ("BG"). Moreover, these classes can be further separated into individual components. For example, multiple CBHs and EGs have been isolated from a variety of bacterial and fungal sources including *Trichoderma reesei* which contains 2 CBHs, i.e., CBHI and CBHII, and at least 2 EGs, i.e., EGI and EGII components. *T. reesei* is also classified by some in the literature as *T. longibrachiatum*. The ratio of CBHI components to EG components (including all of the EG components) in naturally occurring cellulases does not exceed 5:1. For example, see Brown et al., Genetic Control of Environmental Pollutants, Gilbert S. Omenn, Editor, Chapter "Microbial Enzymes and Ligno-Cellulase Utilization", Hollaender Publishing Corp. Variations of this ratio can result from the use of different microorganisms, depending upon the characteristics of the strain, but in any event such ratios do not exceed about 5:1.

The complete cellulase system comprising CBH, EG, and BG is required to efficiently convert crystalline forms of cellulose to glucose. Isolated components are far less effective, if at all, in hydrolyzing crystalline cellulose. Moreover, a synergistic relationship is observed between the cellulase components. That is to say, the effectiveness of the complete/whole system is significantly greater than the sum of the contributions from the isolated components. It has also been suggested by Wood, "Properties of Cellulolytic Systems", *Biochem. Soc. Trans.*, 13, 407–410 (1985), that CBHI and CBHII derived from either *T. reesei* or *P. funiculosum* synergistically interact in solubilizing cotton fibers. On the other hand, Shoemaker et al., *Bio/Technology*, October 1983, disclose that CBHI (derived from *T. reesei*), by itself, has the highest binding affinity but the lowest specific activity of all forms of cellulose.

The substrate specificity and mode of action of the different cellulase components varies from component to component, which accounts for the synergy of the combined components. For example, the mechanism of cellulose breakdown by cellulase is through the combined action of endo- and exoglucanase activity on crystalline cellulase. It is currently accepted that endoglucanase components act on internal β-1,4-glucosidic bonds in regions of low crystallinity of the cellulose thereby creating chain ends which are recognized by CBH components. The CBH components bind preferentially to the non-reducing end of the cellulose to release cellobiose as the primary product. The more non-reducing chain ends, the greater the action of the CBH components. β-Glucosidase components act primarily to relieve end product inhibition and act on the non-reducing ends of cellooligosaccharides, e.g., cellobiose and cellotriose, to give glucose as the sole product.

β-Glucosidases are essential components of the cellulase system and are important in the complete enzymatic breakdown of cellulose to glucose. The β-glucosidase enzymes can catalyze the hydrolysis of alkyl and/or aryl β-D-glucosides such as methyl β-D-glucoside and p-nitrophenyl glucoside, as well as glycosides containing only carbohydrate residues, such as cellobiose. The catalysis of cellobiose is important since the accumulation of cellobiose inhibits cellobiohydrolases, which in turn inhibits the other cellulase components and thus effects the rate of hydrolysis of cellulose to glucose. This product inhibition by cellobiose is caused by the lack of conversion of cellobiose to glucose. Thus, the β-glucosidases play a key role in effecting the conversion of cellulose to glucose.

Since β-glucosidases can catalyze the hydrolysis of a number of different substrates, the use of this enzyme in a variety of different applications is possible. For instance, some β-glucosidases can be used to liberate aroma in fruit by catalyzing various glucosides present therein. Similarly, some β-glucosidases can hydrolyze grape monoterpenyl β-glucosidase which upon hydrolysis, represents an important potential source of aroma to wine as described by G ünata et al, "Hydrolysis of Grape Monoterpenyl β-D-Glucosides by Various β-Glucosidases", *J. Agric. Food Chem.*, Vol. 38, pp. 1232–1236 (1990).

Furthermore, cellulases can be used in conjunction with yeasts to degrade in biomass cellobiose to glucose that yeasts can further ferment into ethanol. This production of ethanol from readily available sources of cellulose can provide a stable, renewable fuel source. The use of ethanol as a fuel has many advantages compared to petroleum fuel products such as a reduction in urban air pollution, smog, and ozone levels, thus enhancing the environment. Moreover, ethanol as a fuel source would reduce the reliance on foreign oil imports and petrochemical supplies.

But the major drawback to ethanol production from biomass is the lack of β-glucosidase in the system to efficiently convert cellobiose to glucose. Therefore, a cellulase composition that contains an enhanced amount of β-glucosidase would be useful in ethanol production.

β-glucosidases are present in a variety of prokaryotic organisms, as well as eukaryotic organisms. The gene encoding β-glucosidase has been cloned from several prokaryotic organisms and the gene is able to direct the synthesis of detectable amounts of protein in *E. coli* without requiring extensive genetic engineering, although, in some cases, coupling with a promotor provided by the vector is required. This often is not the case with eukaryotic genes which lack the Shine-Delgarno sequence for prokaryotic translational initiation and which often contain introns. Such genes can sometimes be expressed and detected after transformation of the eukaryotic host *S. cerevisia,* but many fungal genes fail to be expressed in yeast. Thus, in order to use fungal strains, fungal genes would have to be cloned using methods described herein or by detection with the *T. reesei* bgl1 gene by nucleic acid hybridization.

The contribution and biochemistry of the β-glucosidase component in cellulose hydrolysis is complicated by the apparent multiplicity of enzyme forms associated with *T. reesei* (Enari et al, "Purification of *Trichoderma reesei* and *Aspergillus niger* β-glucosidase", *J. Appl. Biochem.,* Vol. 3, pp. 157–163 (1981); Umile et al, "A constitutive, plasma membrane bound β-glucosidase in *Trichoderma reesei*", *FEMS Microbiology Letters,* Vol. 34, pp. 291–295 (1986); Jackson et al, "Purification and partial characerization of an extracellular β-glucosidase of *Trichoderma reesei* using cathodic run, polyacrylamide gel electrophoresis", *Biotechnol. Bioeng.,* Vol. 32, pp. 903–909 (1988)). These and many other authors report β-glucosidase enzymes ranging in size from 70–80 Kd and in pI from 7.5–8.5. More recent data suggests that the extracellular and cell wall associated forms of β-glucosidase are the same enzyme (Hofer et al, "A monoclonal antibody against the alkaline extracellular β-glucosidase from *Trichoderma reesei*: reactivity with other Trichoderma β-glucosidases", *Biochim. Biophys. Acta,* Vol. 992, pp. 298–306 (1989); Messner and Kubicek, "Evidence for a single, specific β-glucosidase in cell walls from *Trichoderma reesei* QM9414", *Enzyme Microb. Technol.,* Vol. 12, pp. 685–690 (1990)) and that the variation in size and pI is a result of post translational modification and heterogeneous methods of enzyme purification. It is unknown whether the intracellular β-glucosidase species with a pI of 4.4 and an apparent molecular weight of 98,000 is a novel β-glucosidase (Inglin et al, "Partial purification and characterization of a new intracellular β-glucosidase of *Trichoderma reesei*", *Biochem. J.,* Vol. 185, pp. 515–519 (1980)) or a proteolytic fragment of the alkaline β-glucosidase associated to another protein (Hofer et al, supra). In addition, since a major part of the detectable β-glucosidase activity remains bound to the cell wall (Kubicek, "Release of carboxymethyl-cellulase and β-glucosidase from cell walls of *Trichoderma reesei*", *Eur. J. Appl. Biotechnol.,* Vol. 13, pp. 226–231 (1981); Messner and Kubicek, supra; Messner et al, "Isolation of a β-glucosidase binding and activating polysaccharide from cell walls of *Trichoderma reesei*", *Arch. Microbiol.,* Vol. 154, pp. 150–155 (1990)) commercial preparations of cellulase are thought to be reduced in their ability to produce glucose because of relatively low concentrations of β-glucosidase.

To overcome the problem of β-glucosidase being rate limiting in the production of glucose from cellulose supplementation of the cellulolytic system of *Trichoderma reesei* with the β-glucosidase of Aspergillus has been attempted with results indicating an increase in rate of saccharification of cellulose to glucose as disclosed by Duff, *Biotechnol Letters,* 7, 185 (1985). Culturing conditions have also been altered to increase β-glucosidase activity in *Trichoderma reesei* as illustrated in Sternberg et al, *Can. J. Microbiol.,* 23, 139 (1977) and Tangnu et al, *Biotechnol. Bioeng.,* 23, 1837 (1981), and mutant strains obtained by ultraviolet mutation have been reported to enhance the production of β-glucosidase in *Trichoderma reesei*. Although these aforementioned methods increase the amount of β-glucosidase in *Trichoderma reesei,* the methods lack practicality and, in many instances, are not commercially feasible.

A genetically engineered strain of *Trichoderma reesei* that produces an increased amount of β-glucosidases would be ideal, not only to produce an efficient cellulase system, but to further use the increased levels of expression of the bgl1 gene to produce a cellulase product that has increased cellulolytic capacity. Such a strain can be feasibly produced using transformation.

But, in order to transform mutant strains of *Trichoderma reesei,* the bgl1 gene must be first characterized in its amino acid sequence, so that it can be cloned to introduce the specific gene into transformed mutant strains of *Trichoderma reesei.*

Accordingly, it is an object of this invention to characterize the bgl1 gene that encodes for extracellular or cell wall bound β-glucosidase from *Trichoderma reesei,* to clone the bgl1 gene into a plasmid vector that can be used in the transformation process, and to introduce the bgl1 gene into the *Trichoderma reesei* genome in multiple copies, which can be used to generate transformed strains with a significant increase in β-glucosidase activity. Moreover, cellulase compositions that contain increased cellulolytic capacity are also disclosed. In yet another aspect of the present invention, the bgl1 gene can be totally deleted from the *Trichoderma reesei* genome. In addition, altered copies of the bgl1 gene which may change the properties of the enzyme can be reintroduced back into the *Trichoderma reesei* genome. These and other objects are achieved by the present invention as evidenced by the summary of the invention, description of the preferred embodiments, and claims.

SUMMARY OF THE INVENTION

The amino acid sequence of the extracellular or cell wall bound β-glucosidase protein from *Trichoderma reesei* has now been obtained in sufficient detail to enable the bgl1 gene to be cloned into a suitable plasmid vector. The plasmid vector can then be used to transform mutant strains of *Trichoderma reesei,* hereinafter referred to as *T. reesei,* which have multiple copies of the bgl1 gene introduced therein.

Accordingly, in one of its process aspects, the present invention relates to a process for expressing enhanced extracellular β-glucosidase in a filamentous fungus comprising expressing a fungal DNA sequence encoding enhanced β-glucosidase in a recombinant host microorganism, said recombinant host microorganism being a filamentous fungus transformed with an expression vector containing said DNA sequence.

In another process aspect, the present invention relates to a process for expressing cellulases, but not expressing extracellular β-glucosidase in a filamentous fungus.

In yet another process aspect, the present invention relates to a process for expressing an altered extracellular β-glucosidase in a filamentous fungus.

In another aspect, the present invention is directed to the amino acid sequence of extracellular β-glucosidase from *Trichoderma reesei.*

In yet another aspect, the present invention is directed to use of the entire or partial oligonucleotide sequence of an extracellular β-glucosidase gene as probes to identify and clone out the equivalent bgl1 gene from other filamentous fungi.

In one of its composition aspects, the present invention is directed to novei and useful transformants of *Trichoderma reesei,* which can be used to produce fungal cellulase compositions, especially fungal cellulase compositions enriched in β-glucosidase or depleted of β-glucosidase. Also contemplated in the present invention is the alteration of the bgl1 gene and the introduction of the altered bgl1 gene into *T. reesei* to produce transformants which can also be used to produce altered fungal cellulase compositions.

In another composition aspect, the present invention is directed to fungal cellulase compositions prepared via the transformed *Trichoderma reesei* strains.

BRIEF DESCRIPTION OF THE DRAWINGS

FIG. 1 is the nucleotide sequence and deduced primary amino acid structure of the entire *T. reesei* bgl1 gene (SEQ ID NO: 1).

FIG. 2 is a schematic representation of the vector pSASβ-glu.

FIG. 3 represents a Northern blot of RNA isolated from the transformed strains of *Trichoderma reesei* following induction with sophorose using the probes of cbh2 and a 700 bp fragment of bgl1 cDNA.

FIG. 4 represents an autoradiograph of Hind III digested genomic DNA from a *T. reesei* overproducing strain and transformants of pSASβ-Glu, blotted and probed with the 700 bp β-Glu probe.

FIG. 5 represents a curve illustrating Avicel hydrolysis using the dosage, substrate:enzyme of 80:1 from an enriched recombinant β-glucosidase composition produced by the present invention.

FIG. 6 represents a curve illustrating PSC hydrolysis using the dosage, substrate:enzyme of 300:1 from an enriched recombinant β-glucosidase composition produced by the present invention.

FIG. 7 represents a curve illustrating the rate of hydrolysis of a cellulosic diaper derived fibers using an enriched recombinant β-glucosidase composition produced by the present invention.

FIG. 8 is an autoradiograph of *Aspergillus nidulans* and *Neurospora crassa* genomic DNA digested with Hind III and Eco RI, blotted and probed with a DNA fragment containing the bgl1 gene of *Trichoderma reesei*.

DETAILED DESCRIPTION OF THE PREFERRED EMBODIMENTS OF THE INVENTION

As used herein, the term "enhanced extracellular β-glucosidase" or "enhanced β-glucosidase" means that at least one additional copy of a gene encoding for extracellular β-glucosidase has been introduced into the genome.

As used herein, the term "devoid of the bgl1 gene" means that the bgl1 gene has been depleted from the genome and therefore cannot be expressed by the recombinant host microorganism.

The term "altered β-glucosidase" or "altered β-glucosidase gene" means that the amino acid sequence has been altered in the gene by removing, adding, and/or manipulating the amino acid sequence.

The term "by recombinant means" denotes that a microorganism has been transformed that contains a DNA molecule created in a test-tube by ligating together pieces of DNA that are not normally contiguous.

More specifically, the present invention relates to the isolation and characterization of the bgl1 gene coding for the extracellular or cell wall bound protein from *Trichoderma reesei*, hereinafter referred to as *T. reesei*, and the specific nucleotide and amino acid sequence of this gene. The bgl1 gene is further cloned into plasmid vectors, which are further used to produce transformed strains having extra copies of the bgl1 gene inserted therein. These transformants are then used to produce cellulase compositions having increased β-glucosidase activity and thus enhanced cellulolytic degradation. Besides enhancing cellulolytic degradation by inserting extra copies of the bgl1 gene into *T. reesei* strains, it is also contemplated by the present invention to produce transformed strains that are completely devoid of the bgl1 gene.

Also contemplated by the present invention is the manipulation of the amino acid sequence in the bgl1 gene itself. Alteration of the active sites on this enzyme may lead to a variety of different changes in catalytic conversion. For example, since β-glucosidase has both hydrolase and transferase activity, alteration of the amino acid sequence may result in the removal of hydrolase activity and an increase in transferase activity and, thus, facilitate the synthesis of β1–4 oligo-dextrins. Moreover, manipulation of the amino acid sequence of β-glucosidase may result in further changes in the system, such as different pH optima, different temperature optima, altered catalytic turn over rate (Vmax), altered affinity (Km) for cellobiose leading to an increased affinity for cellobiose or a decreased affinity for cellobiose resulting in a slower or zero rate of reaction, altered product inhibition profile such that lower or higher levels of glucose will inhibit β-glucosidase activity, and the like.

Moreover, the entire oligonucleotide sequence of the extracellular β-glucosidase gene in *T. reesei* or a portion thereof can also be labeled and used as a probe to identify and clone out the equivalent bgl1 gene in other filamentous fungi.

Generally, the present invention involves the isolation of the bgl1 gene from *T. reesei* by identifying a 700 bp CDNA fragment of the gene which is then used as a probe to identify a single 6.0 kb band on a Southern blot of Hind III digested genomic DNA from *T. reesei*. This 6.0 kb fragment is then cloned into a pUC plasmid and a series of mapping experiments are performed to confirm that the entire bgl1 gene is contained in this fragment. The nucleotide sequence is then determined on both strands and the position of two introns is also confirmed by sequence analysis of bgl1 cDNA subclones spanning the intron/exon boundaries. After isolation of the bgl1 gene, additional bgl1 gene copies are then introduced into *T. reesei* strains to increase the expression of β-glucosidase. In contrast, the entire bgl1 gene can also be deleted from the *T. reesei* genome, thereby producing transformants that express other cellulases.

The isolation of the bgl1 gene from *T. reesei* involves the purification of extracellular β-glucosidase, chemical and proteolytic degradation of this protein, isolating and sequencing of the proteolytic fragments and design of synthetic oligomer DNA probes using the protein sequence. The oligomeric probes are then further used to identify a 700 bp β-glu cDNA fragment which can be labeled and employed to later identify a fragment that contains the entire bgl1 gene within the fragment from digested genomic DNA from *T. reesei*.

To identify a feasible cDNA fragment that can be used as a probe for future analysis, total RNA is first isolated from *T. reesei* mycelia and polyadenylated RNA isolated therefrom. The polyadenylated RNA is then used to produce a CDNA pool which is then amplified using specific oligonucleotide primers that amplify only the specific cDNA fragment encoding the *T. reesei* bgl1 gene.

More specifically, total RNA is first isolated from a starting strain of *T. reesei*. The starting strain employed in the present invention can be any *T. reesei* cellulase production strain that is known in the art. This cellulase producing strain is generally developed by ordinary mutagenesis and selection methods known in the art from any *T. reesei* strain. Confirmation that cellulases are over-producing in the strain can be performed by using known analysis methods.

A mycelial inoculum from the *T. reesei* over production strain, grown in an appropriate growth medium, is added to a basal medium and incubated for a period of between 50–65 hours at a temperature between 25° C. to 32° C., preferably 30° C. Fresh basal medium can be replaced during this incubation period. The culture medium is then centrifuged, and the mycelia is isolated therefrom and washed. The mycelia is then resuspended in a buffer to permit growth thereof and 1 mM sophorose (a β,1–2 dimer of glucose) is added to the mycelia to induce the production of cellulase enzymes. The mycelia preparation is then incubated for an additional time period, preferably 18 hours at 30° C. prior to harvesting. Total RNA can then be further isolated from the mycelia in this culture.

Total RNA can be isolated by a variety of methods known in the art, such as proteinase K lysation, followed by phenol:chloroform extraction, guanidinium thiocyanate extraction, followed by cesium chloride gradients, guanidine hydrochloride and organic solvent extraction, and the like. It is preferable to isolate total RNA via the procedure described by Timberlake et al in "Organization of a Gene Cluster Expressed Specifically in the Asexual Spores of *A. nidulans,*" *Cell,* 26, pp. 29–37 (1981). Generally, this procedure involves extraction of RNA from the mycelia, which is isolated from the culture medium via filtration, with an extraction buffer, TE-saturated phenol and chloroform. The aqueous phase is then removed and the organic phase is reextracted with the extraction buffer. The reextracted aqueous phase is then heated in a water bath at a temperature between about 60° C. to 80° C., preferably 68° C. to release the RNA trapped in polysomes and at the interface. All of the extracted aqueous phases are then pooled, centrifuged and reextracted with phenol-chloroform until there is no longer any protein at the interface. The RNA is further precipitated with 2 M lithium acetate and pelleted via centrifugation before it is resuspended in DEP-water containing an RNase inhibitor.

The total RNA are then fractionated on 1% formaldehyde-agarose gels, blotted to Nytran® membranes, and probed using a fragment of the *T. reesei* cbh2 gene as a probe to determine whether the genes encoding the enzymes of the cellulase system in the *T. reesei* preparation is indeed induced by addition of the sophorose. Basically, the probe used in the present invention is derived from a CBHII clone produced by methods known in the art. For more specific detail of how the clone was produced see Chen et al, "Nucleotide Sequence and Deduced Primary Structure of Cellobiohydrolase II from *Trichoderma reesei,*" *Bio/Technology,* Vol. 5 (March 1987). Site directed mutagenesis was performed on the cDNA clone and a Bgl II site was placed at the exact 5' end of the open reading frame and a Nhe I site at the exact 3' end. The Bgl II and Nhe I restriction fragment containing CBHII coding sequence was further cloned into a pUC218 phagemid. The CBHII gene was further cut and gel isolated prior to adding a label.

The results of the Northern blot probed with the cbh2 probe indicated that the level of cbh2 specific mRNA reached a peak at 14–18 hours post induction. From this data it can be inferred that the entire cellulase complex including β-glucosidase is induced at this time. The total RNA from 14, 18 and 22 hours is then pooled.

After pooling the specific fractions of total RNA, polyadenylated mRNA is further isolated from the total RNA. Postranscriptional polyadenylation is a common feature of the biogenesis of most eukaryotic mRNAs. The newly synthesized mRNAs have long poly(A) tracts which tend to shorten as mRNAs age. The newly synthesized polyadenylated MRNA is further isolated from total RNA by methods known in the art. These methods include the use of oligo (dT)-cellulose, poly(U) Sepharose, adsorption to and elution from poly(U) filters or nitrocellulose membrane filters, and the like. It is preferable to use oligo(dT) cellulose chromatography in isolating mRNA following the procedure described by Maniatis et al, *Journal of Molecular Cloning Techniques,* Cold Spring Harbor Press (1982). More specifically, fractions of total RNA are placed over the chromatographical resin, and mRNA is eluted therefrom with an elution buffer. The RNA which binds to the column is enriched for RNAs containing poly(A) tails and, therefore, eliminates contaminants, such as rRNA and partially degraded mRNAs. It is important that the purification be carried out successfully such that when cDNA is synthesized from the mRNA, higher yields of first strand DNA and less spurious copying of nonmessenger RNAs occurs.

Total RNA and polyadenylated RNA from the preparations were further fractionated on 1% formaldehyde gels, blotted to Nytran® membranes and analyzed to confirm that the enzymes in the cellulase complex were being induced as polyadenylated mRNA.

After isolating polyadenylated mRNA from total RNA, complementary DNA or cDNA is synthesized therefrom. The first strand of cDNA is synthesized using the enzyme RNA-dependent DNA polymerase (reverse transcriptase) to catalyze the reaction. Avian reverse transcriptase which is purified from the particles of an avian retrovirus or murine reverse transcriptase, which is isolated from a strain of *E. coli* that expresses a cloned copy of the reverse transcriptase gene of the Moloney murine leukemia virus can be used in the present invention. However, it is preferable to use the Moloney murine leukemia virus (M-MLV) reverse transcriptase to synthesize first strand cDNA from the polyadenylated mRNA population. The amount of cloned M-MLV reverse transcriptase may vary depending on the amount of polyadenylated mRNA used in the synthesis reaction. Usually, about 200 U/μl of the reverse transcriptase is used per 2 to 10 μg of mRNA per reaction.

Also present in the synthesis mixture is a primer to initiate synthesis of DNA. For cloning of cDNAs, any primer can be used, but it is preferable to use oligo(dT) containing 12–18 nucleotides in length, which binds to the poly(A) tract at the 3' terminus of eukaryotic cellular mRNA molecules. The primer is added to the reaction mixture in large molar excess so that each molecule of mRNA binds several molecules of oligo(dT)$_{12-18}$. It is preferable to use about 12.5 μg of primer having a concentration of 0.5 mg/ml.

Besides the enzyme and primer, a buffer and dNTP mix containing DATP, dCTP, dGTP, and dTTP at a final concentration of 500 μM each usually completes the reaction cocktail. Any buffer can be used in the present invention for first strand CDNA synthesis that is compatible with this synthesis. It is preferable to use a buffering system consisting of 250 mM Tris-HCl (pH 8.3), 375 mM KCl, 15 mM MgCl$_2$, and 50 mM dithiothreitol. Generally, about 500 μl of buffer completes the synthesis solution.

After the first strand is synthesized, the second strand of cDNA may be synthesized by a variety of methods known in the art, such as hairpin-primed synthesis by denaturing the cDNA:mRNA complex, adding the Klenow fragment of *E.coli* DNA polymerase or reverse transcriptase, and then digesting the hairpin loop with nuclease S1 to obtain a double-stranded cDNA molecule, the Okayama and Berg method, the Gubler and Hoffman method, and the like. The Okayama and Berg method uses *E. coli* RNase H to randomly nick the MRNA, and the RNA is replaced in the nick translation reaction by catalysis with *E. coli* DNA polymerase I. In the Okayama and Berg method, mRNA is used to prime synthesis by the *E. coli* DNA polymerase I.

The preferred method to synthesize the second strand of cDNA is a modified method of the Gubler and Hoffman procedure. This procedure uses *E. coli* RNase H, DNA Polymerase I, and DNA Ligase to form the second strand. Actually, two different methods of proceeding with the second strand synthesis can be used in the present invention. The first procedure uses RNase H to attack the RNA:DNA hybrid in a random fashion, producing nicks in addition to those produced by reverse transcriptase. If enough additional nicks are introduced into the RNA at the 5' end of the message before second strand synthesis commences, fragments may be produced that are too short to remain hybridized; thus, they will not be able to serve as primers. In addition, the 5'-most RNA oligomer which primes second strand DNA synthesis will continue to be degraded until only two ribonucleotides remain at the 5' end of the second strand DNA. These are substrates for the polymerase I RNase H activity, and the remaining nucleotides will be removed. This also leaves the 3' end of the first strand cDNA single stranded, making it a substrate for the 3' exonuclease activity of Polymerase I. The result is a population of cDNAs, which are blunt-ended.

An alternative method relies on M-MLV reverse transcriptase to produce nicks 10 to 20 bases from the 5' end of the RNA in the hybrid. DNA polymerase I is then used for synthesis. Generally, about 500 units at a concentration of 10 U/µl of DNA polymerase I is used. After second strand synthesis, RNase H is added after removal of the DNA polymerase I to produce a duplex, which is entirely DNA, except for the surviving capped RNA 5' oligonucleotide.

The second-strand synthesis by either procedure set forth above usually takes place in the presence of a buffer and dNTP mix. Any buffering system that is known in the art for second strand cDNA synthesis can be used; however, it is preferable to use a buffering system containing 188 mM Tris-HCl, pH 8.3, 906 mM KCl, 100 mM $(NH_4)_2SO_4$, 46 mM $MgCl_2$, 37.5 mM dithiothreitol, and 1.5 mM NAD. The dNTP mix preferably contains 10 mM DATP, 10 mM dCTP, 10 mM dGTP, and 10 mM dTTP.

The second strand synthesis is carried out under known procedures set forth in the art. The preferred method and reagent used to synthesize cDNA in the present invention is the BRL cDNA Synthesis System® (Bethesda Research Laboratories, Gaithersburg, Md.).

At this point a pool of cDNAs, a small portion of which code for the bgl1 gene, is present after second strand synthesis. Since amplification of only the specific bgl1 gene fragment in the cDNA pool is crucial, specific primers were designed to amplify the cDNA fragment encoding the *T. reesei* bgl1 gene in the polymerase chain reaction (PCR). The primers used are degenerate primers designed to hybridize to the cDNA of the bgl1 gene encoding the N-terminus and an internal CNBr fragment. These primers were designed based on examining the genetic code for the selected amino acids of the region targeted for amplification of mature β-glucosidase and choosing regions, which will tolerate some degree of degeneracy. Codon bias in *T. reesei* for various other cellulase genes such as cbh1, cbh2, egl1, and the like was also taken into account when designing the oligonucleotide primers. More specifically, codon bias is based on various genes in the strain *T. reesei* which display a preferred nucleotide triplet encoding different amino acids. By analyzing this codon bias one can assimilate that a particular nucleotide sequence coding for an amino acid would be preferred. For example, the cbh1, cbh2 and egl1 genes from *T. reesei* prefer the GCC coding for the amino acid alanine. Thus, when designing an oligonucleotide probe, the GCC sequence would be the preferred choice for alanine, rather than the other triplets of GCA, GCG or GCU.

After selection of an N-terminal region and an internal region for amplification purposes, the primers were designed by inserting a non-specific base inosine into the wobble position of the primer for the N-terminus and using a pool of sixteen variable primer sequences for the internal primer. Basically, the creation of these degenerate primers are described by Compton in "Degenerate Primers For DNA Amplification" and Lee et al in "cDNA Cloning Using Degenerate Primers" in *PCR Protocols: A Guide to Methods and Applications*, published by Academic Press (1990).

Using the primers described above, the cDNA sequences encoding the amino terminal region of the bgl1 gene is then selectively amplified using PCR. The amplification method consists of an initial, denaturing cycle of between about 5 to 15 minutes at 95° C., followed by a 1–7 minutes annealing step at a temperature between 45° C. and 55° C. and a 5–15 minutes polymerization cycle at 65° C. It is preferable, however, to use a 10 minute initial denaturing cycle, followed by 2 minutes of annealing at 50° C. and a 10 minute polymerization cycle at the aforedescribed temperatures.

The amplified fragment is then further identified via gel electrophoresis as a 700 bp CDNA segment. The amplified pool of cDNAs is then further fractionated on a polyacrylamide gel to obtain a more purified fragment of the 700 bp cDNA for cloning purposes. After elution of the cDNA fragment from the gel, the 700 bp cDNA fragments are then cloned into phagemid vectors. Any cloning vector can be used to clone the cDNA bgl1 gene fragments, such as pUC18, pUC19, pUC118, pUC119, pBR322, PEMBL, pRSA101, pBluescript, and the like. However, it is preferable to use the cloning vectors pUC218 and pUC219, which are derived from pUC18 and pUC19 by insertion of the intergenic region of M13. The cloning vectors with the cDNA fragments containing the bgl1 gene are then used to transform *E. coli* strain JM101. After transformation, the positive colonies are picked and DNA isolated therefrom using chloroform:phenol extraction and ethanol precipitation methods.

The nucleotide sequence of the subcloned cDNA 700 bp fragments is then determined by the dideoxy chain termination method described by Sanger et al using a Sequenase® reagent kit provided by U.S. Biochemicals.

From this nucleotide sequence it was determined that the subcloned 700 bp cDNA segment contained an open reading frame encoding 150 amino acids that overlapped a number of other sequenced peptides that were obtained following CNBr and proteolytic degradation of purified *T. reesei* β-glucosidase. Thus, it was confirmed that the cloned sequences encoded for the extracellular *T. reesei* β-glucosidase protein.

The cloning of the genomic version of the entire β-glucosidase gene was then undertaken by labelling the 700 bp bgl1 cDNA fragment with $^{32}P$ using the methods to label oligonucleotides described by Maniatis et al, supra. This probe is used to identify a 6.0 kb band on a Southern blot of Hind III digested genomic DNA from *T. reesei*.

The genomic DNA from *T. reesei* is prepared for Southern analysis by deproteinizing the genomic DNA, followed by treatment with ribonuclease A. The prepared genomic DNA is then cut with a variety of restriction enzymes such as Eco RI, Hind III and the like, Southern blotted and hybridized with the 700 bp cDNA labelled fragment of the bgl1 gene. From this analysis, it was determined that Hind III was the restriction enzyme of choice that can be used to locate the 6.0 kb fragment.

Hind III is then added to genomic DNA from the strain *T. reesei* and DNA is extracted therefrom. A sample from this digestion is run on an agarose gel and fractionated electrophoretically. The gel is then Southern blotted and probed with the 700 bp cDNA probe. A 6.0 kb band was then identified on the Southern blot of Hind III digested genomic DNA. The remaining Hind III genomically digested DNA was then subjected to preparative electrophoresis and DNA ranging in size from about 5.0 kb to 7.0 kb was eluted therefrom and cloned into a phagemid vector and transformed with *E. coli* JM101 to create a library. Any phagemid vector can be used such as those described above, however it is preferable to use pUC218. The colonies that resulted from the transformation were then subject to colony hybridization using the 700 bp β-glu cDNA fragment as a probe to identify those colonies that contained the cloned genomic DNA coding for bgl1. The positive colonies from the transformation are then picked and the DNA isolated therefrom by methods known in the art.

The isolated DNA from such a positive is then digested with various restriction enzymes, both singly and in various combinations, and then subjected to agarose gel electrophoresis. The resultant banding pattern is then used to construct a restriction map of the cloned 6.0 kb genomic DNA from *T. reesei*. Enzymes used in the digestion include Eco RI, Sst I, Kpn I, Sma I, Bam HI, Xho 1, Bgl II, Cla I, Xba I, Sal I, Pst I, Sph I, Hind III, Bal I, Pvu II and the like.

The same gel is then subject to Southern blot analysis using the same 700 bp bgl1 cDNA as a probe to identify which genomic restriction fragments shared homology with the bgl1 cDNA. Since the position of these fragments is known relative to the restriction map of the 6.0 kb genomic fragment and also since the size of the β-glucosidase protein (74 kd) gives an estimated length of the gene as 2.1 kb (average molecular weight of an amino acid is 105 daltons which is 705 amino acids, which in turn is equal to 2,100 bp), then the mapping experiments confirmed that the entire bgl1 gene is contained on the genomic Hind III clone.

Pvu II and Bal I restriction fragments ranging in size from 600 bp to 1500 bp hybridized with the 700 bp cDNA bgl1 clone and were thus chosen for subcloning into pUC218 phagemids. The Pvu II and Bal I subclones were sequenced and the overlapping sequences of the subclones aligned until a single contiguous sequence totaling 3033 bp was obtained within which the nucleotide sequence of the bgl1 gene was determined on both strands and the position of two small introns was confirmed by sequence analysis of bgl1 cDNA subclones spanning the intron/extron boundaries.

The nucleotide sequence was determined using the methods of Sanger et al, described above. The amino acid sequence is also deduced as set forth in FIG. 1 (SEQ ID NO: 1; SEQ ID NO: 2).

The nucleotide sequence and deduced primary amino acid sequence of the entire *T. reesei* bgl1 gene is set forth in FIG. 1 (SEQ ID NO: 1SEQ ID NO:2). The predicted molecular weight of the encoded β-glucosidase protein is 74,341. A 31 amino acid peptide precedes the mature amino terminus of β-glucosidase as deduced from the amino terminal peptide sequence. Within this peptide, there are three potential signal peptidase recognition sites consisting of Ala-X-Ala.

The primary amino acid sequence of B-glucosidase shows 7 potential N-linked glycosylation sites at positions 208, 310, 417, and 566, which shows the consensus Asn-X-Ser/Thr-X where X is not a proline. However, sites at positions 45, 566, and 658 have a proline residue in the consensus sequence and may or may not be glycosylated.

No unusual codon bias is observed in the bgl1 gene when compared to other cellulase genes. The bgl1 coding region is interrupted by two short introns of 70 bp and 64 bp, respectively. Both introns have splice site donor, splice acceptor, and lariat branch acceptor sites that show homology to the consensus splice signals emerging from *T. reesei* and other filamentous fungi.

Since the bgl1 gene in the strain *T. reesei* is identified and can be cloned, transformation of the bgl1 gene is the next step performed to produce a transformant that has extra copies of the bgl1 gene.

A selectable marker must first be chosen so as to enable detection of the transformed fungus. Different selectable markers may be used including argB from *A. nidulans* or *T. reesei,* amdS from *A. nidulans,* and pyr4 from *Neurospora crassa, A. nidulans* or *T. reesei.* The selectable marker can be derived from a gene, which specifies a novel phenotype, such as the ability to utilize a metabolite that is usually not metabolized by *T. reesei* or the ability to resist toxic shock effects of a chemical or an antibiotic. Also contemplated within the present invention are synthetic gene markers that can be synthesized by methods known in the art. Transformants can then be selected on the basis of the selectable marker introduced therein. It is preferable to use the amdS gene as a selectable marker that encodes the enzyme acetamidase, which allows transformant cells to grow on acetamide as a nitrogen source.

The host strain used should be mutants of *T. reesei,* which lack or have a nonfunctional gene or genes corresponding to the selectable marker chosen. For example, if the selectable marker of argB is used, then a specific arg⁻ mutant strain is used as a recipient in the transformation procedure. Other examples of selectable markers that can be used in the present invention include the genes trp, pyr4, trp1, oliC31, Bm1, pkiA, niaD, leu, and the like. The corresponding recipient strain must, therefore, be a mutant strain such as Trp⁻, Pyr⁻, Leu⁻, and the like.

The mutant strain is derived from a starting host strain, which is any *T. reesei* strain. However, it is preferable to use a *T. reesei* over-producing mutant strain, described previously, since this strain secretes high amounts of proteins and, in particular, high amounts of cellulase enzymes. This mutant strain is then used in the transformation process.

The mutant strain of *T. reesei* can be prepared by a number of techniques known in the art, such as the filtration enrichment technique described by Nevalainen in "Genetic improvement of enzyme production in industrially important fungal strains", Technical Research Center of Finland, Publications 26 (1985). Another technique to obtain the mutant strain is to identify the mutants under different growth medium conditions. For instance, the arq⁻ mutants can be identified by using a series of minimal plates supplied by different intermediates in arginine biosynthesis. Another example is the production of pyr⁻ mutant strains by subjecting the strains to fluoroorotic acid (FOA). Strains with an intact pyr4 gene grow in an uridine medium and are sensitive to fluoroorotic acid, and, therefore, it is possible to select pyr4⁻ mutant strains by selecting for FOA resistance. It is preferable to use an amdS mutant strain of *T. reesei*.

The chosen selectable marker is then cloned into a suitable plasmid. Any plasmid can be used in the present invention for the cloning of the selectable marker such as pUC18, pBR322, and the like. However, it is preferable to use pUC100. The vector is created by digesting pUC100 with the restriction enzyme SmaI, and the 5' phosphate groups are then removed by digestion with calf alkaline phosphatase. The fragment vector is then purified by gel electrophoresis followed by electroelution from the isolated gel slice. The amds gene from *A. nidulans* is isolated as a 2.4 kb SstI restriction fragment following separation of the vector sequences via known procedures such as those described by Hynes et al, *Mol. Cell. Biol.*, 3, pp. 1430–1439 (1983). The 2.4 Kb SstI amds fragment and the 2.7 Kb pUC100 vector fragment are then ligated together, and the ligation mix is then transformed and propagated in the *E. coli* host strain JM101.

Any plasmid can be used in the present invention for the insertion of the bgl1 gene, but it is preferable to use the pSAS plasmid.

pSASβ-glu is constructed by digesting PSAS with the restriction enzyme Hind III and purifying the linear fragment via gel electrophonesis and electroelution. Into this Hind III treated PSAS vector fragment is ligated a 6.0 Kb Hind III fragment of *T. reesei* genomic DNA that contained all of the coding region of the bgl1 gene along with the sequence necessary for the genes transcription and translation. FIG. 2 illustrates the construction of pSASβ-glu.

It is also possible to construct vectors that contain at least one additional copy of the bgl1 gene and to construct vectors in which the amino acid sequence of bgl1 gene has been altered by known techniques in the art such as site directed mutagenesis, PCR methods, and chemical mutation methods. In another embodiment, the bgl1 gene can be totally deleted and may be replaced with other known *T. reesei* genes. Potentially any *T. reesei* gene which has been cloned and thus identified in the genome, can replace the bgl1 gene using the techniques described herein. Alternatively, no replacement of the bgl1 gene may be undertaken.

After a suitable vector is constructed, it is used to transform various *T. reesei* strains. Since the permeability of the cell wall in *T. reesei* is very low, uptake of the desired DNA sequence, gene or gene fragment is at best minimal. To overcome this problem, the permeability of the cell wall can be increased or the DNA can be directly shot into the cells via a particle gun approach. In the particle gun approach, the DNA to be incorporated into the cells is coated onto micron size beads and these beads are literally shot into the cells leaving the DNA therein and leaving a hole in the cell membrane. The cell then self-repairs the cell membrane leaving the DNA incorporated therein. Besides this aforedescribed method, there are a number of methods to increase the permeability of *T. reesei* cells walls in the mutant strain (i.e., lacking a functional gene corresponding to the used selectable marker) prior to the transformation process.

One method involves the addition of alkali metal ions at high concentrations to *T. reesei* cells. Any alkali metal or alkaline earth metal ion can be used in the present invention; however, it is preferable to use either $CaCl_2$ or lithium acetate and more preferable to use lithium acetate. The concentration of the alkali metal ions may vary depending on the ion used, and usually between 0.05 M to 0.4 M concentrations are used. It is preferable to use about a 0.1 M concentration.

Another method that can be used to induce cell wall permeability to enhance DNA uptake in *T. reesei* is to resuspend the cells in a growth medium supplemented with sorbitol and carrier calf thymus DNA. Glass beads are then added to the supplemented medium, and the mixture is vortexed at high speed for about 30 seconds. This treatment disrupts the cell walls, but may kill many of the cells.

Yet another method to prepare *T. reesei* for transformation involves the preparation of protoplasts. Fungal mycelium is a source of protoplasts, so that the mycelium can be isolated from the cells. The protoplast preparations are then protected by the presence of an osmotic stabilizer in the suspending medium. These stabilizers include sorbitol, mannitol, sodium chloride, magnesium sulfate, and the like. Usually, the concentration of these stabilizers varies between 0.8 M to 1.2 M. It is preferable to use about a 1.2 M solution of sorbitol in the suspension medium.

Uptake of the DNA into the host mutant *T. reesei* strain is dependent upon the calcium ion. Generally, between about 10 mM $CaCl_2$ and 50 mM $CaCl_2$ is used in an uptake solution. Besides the need for the calcium ion in the uptake solution, other items generally included are a buffering system such as TE buffer (10 mM Tris, pH 7.4; 1 mM EDTA) or 10 mM MOPS, pH 6.0 buffer (morpholinepropanesulfonic acid), and polyethylene glycol (PEG). The polyethylene glycol acts to fuse the cell membranes, thus permitting the contents of the mycelium to be delivered into the cytoplasm of the *T. reesei* mutant strain and the plasmid DNA is transferred to the nucleus. This fusion frequently leaves multiple copies of the plasmid DNA tandemly integrated into the host chromosome. Generally, a high concentration of PEG is used in the uptake solution. Up to 10 volumes of 25% PEG 4000 can be used in the uptake solution. However, it is preferable to add about 4 volumes in the uptake solution. Additives such as dimethyl sulfoxide, heparin spermidine, potassium chloride, and the like may also be added to the uptake solution and aid in transformation.

Usually a suspension containing the *T. reesei* mutant cells that have been subjected to a permeability treatment or protoplasts at a density of $10^8$ to $10^9$/ml, preferably $2 \times 10^8$/ml, are used in transformation. These protoplasts or cells are added to the uptake solution, along with the desired transformant vector containing a selectable marker and other genes of interest to form a transformation mixture.

The mixture is then incubated at 4° C. for a period between 10 to 30 minutes. Additional PEG is then added to the uptake solution to further enhance the uptake of the desired gene or DNA sequence. The PEG may be added in volumes of up to 10 times the volume of the transformation mixture, preferably, about 9 times. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only and, therefore, contains no uridine. The subsequent colonies were transferred and purified on a growth medium depleted of sorbitol.

In order to ensure that the transformation took place by the above-described methods, further analysis is performed on the transformants such as Southern blotting and autoradiography. Using the same basic procedures set forth above, the entire bgl1 gene can be deleted from a vector and transformed into *T. reesei* strains or the bgl1 gene can be altered and transformed into *T. reesei* strains.

After confirmation that the transformed strains contained at least one additional copy of the bgl1 gene, an altered bgl1 gene or the transformants contained a deleted bgl1 gene, the strains are further cultured under conditions permitting these transformants to propagate. The transformants can then be isolated from the culture media and used in a variety of applications which are described below. Alternatively, the transformants can be further fermented and a recombinant fungal cellulase composition can be isolated from the culture media. Since, for example, the transformants produced by the present invention can express enhanced, deleted or altered extracellular β-glucosidase in the fermentation medium, fungal cellulase compositions can be isolated from medium. Usually, the isolation procedure involves centrifuging the culture or fermentation medium containing the transformants and filtering by ultrafiltration the supernatant to obtain a recombinantly produced fungal cellulase composition. Optionally, an antimicrobial agent can be further added to the composition prior to use in the variety of applications described below. Examples of microbial agents that can be added are sodium azide, sodium benzoate and the like.

Confirmation that the transformants produced by the process of the present invention had enhanced activity on cellobiose, the following experiment was performed. In this experiment 50 mg of cellobiose which was suspended in 1.0 ml of phosphate buffer (pH 5.0) and was reacted with the fermentation product produced by the transformant (65.5 mg/ml protein) using a fermentation product from a normal nonmutant *T. reesei* strain as a control (135.0 mg/ml protein). The results of cellobiase activity under conditions of initial rate, are set forth in Table I below:

TABLE I

| product | Protein( mg/ml) | Activity on Cellobiose μmole glucose mg protein |
|---|---|---|
| control | 135.0 | 6 |
| product produced by the present invention | 65.5 | 33 |

The results from this experiment indicate that the fermentation product produced by the transformants of the present invention has over five times the specific activity on the substrate, cellobiose, compared to a nonmutant *T. reesei* control strain.

Moreover, FIGS. 6 and 7 confirm that hydrolysis is enhanced for the substrates Avicel and PSC (note: PSC is a phosphoric acid swollen cellulose obtained by treating Avicel with phosphoric acid) using 1.0% enzyme/substrate. In the experiment, PSC or Avicel was suspended in 2 mls of 50 mM sodium acetate buffer, pH 4.8, and incubated at 40° under non-agitated conditions for up to 24 hours. Soluble reducing sugar was measured by the method of Nelson and Somogyi. From these figures it is further demonstrated that the enhanced recombinant β-glucosidase fermentation product produced from transformants according to the present invention, has an increased rate and extent of hydrolytic activity on the various substrates compared to the standard Cyt-123 control (on average 20% higher activity). The Cyt-123 control is the product obtained from a *T. reesei* cellulase production strain subjected to fermentation on an industrial scale.

The enriched transformants can be used in a variety of different applications. For instance, some β-glucosidases can be further isolated from the culture medium containing the enhanced transformants and added to grapes during wine making to enhance the potential aroma of the finished wine product. Yet another application can be to use β-glucosidase in fruit to enhance the aroma thereof. Alternatively, the isolated recombinant fermentation product containing enhanced β-glucosidase can be used directly in food additives or wine processing to enhance the flavor and aroma.

Since the rate of hydrolysis of cellulosic products is increased by using the transformants having at least one additional copy of the bgl1 gene inserted into the genome, products that contain cellulose or heteroglycans can be degraded at a faster rate and to a greater extent. Products made from cellulose such as paper, cotton, cellulosic diapers and the like can be degraded more efficiently in a landfill. FIG. 7 illustrates the use of an increased β-glucosidase preparation isolated from the fermentation medium containing transformants having at least one additional copy of the bgl1 gene inserted into the genome compared to a non-enhanced Cyt 123 standard (defined above) on a cellulosic diaper product. This hydrolysis experiment was performed using 0.4 mg of the standard and the fermentation product per 100 mg of substrate (the cellulosic diaper). The experiment was run at 50° C. over a period of five hours and the glucose concentration was measured, in duplicate, at various time intervals. This curve illustrates an increased rate of hydrolysis for the product produced by the fermentation product derived from the transformant having additional copies of bgl1, compared to the standard. It was also determined that the diaper derived fibers were about 14% insoluble in aqueous solution. Thus, the fermentation product obtained from the transformants or the transformants alone can be used in compositions to help degrade by liquefaction a variety of cellulose products that add to overcrowded landfills.

Simultaneous saccharification and fermentation is a process whereby cellulose present in biomass is converted to glucose and, at the same time and in the same reactor, yeast strains convert the glucose into ethanol. Yeast strains that are known for use in this type of process include *B. clausenii, S. cerevisiae, Cellulolyticus acidothermophilium, C. brassicae, C. lustinaniae, S. uvarum, Schizosaccharomyces pombe* and the like. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, one major problem encountered in this process is the lack of β-glucosidase in the system to convert cellobiose to glucose. It is known that cellobiose acts as an inhibitor of cellobiohydrolases and endogluconases and thereby reduces the rate of hydrolysis for the entire cellulase system. Therefore, the use of increased β-glucosidase activity to quickly convert cellobiose into glucose would greatly enhance the production of ethanol. To illustrate this point, cytolase 123 and the fermentation product produced by the transformants (normalized to cytolase on a total protein basis) according to the present invention under fermentation conditions were compared for their ability to hydrolize crude paper fractions composed of 50–60% cellulosics from a fiber fraction (RDF) of municipal solid waste (MSW). Such suspensions were in 50 mM sodium acetate buffer, pH 4.8 to 5.0, and equilibrated at 30° C. The flasks were then dosed with 4% *Saccharomyces cerevisiae* and sampled periodically to 80 hours. The ethanol production yield was then measured. The following Table II illustrates that increased ethanol production is possible using the increased β-glucosidase preparation from the present invention using municipal solid waste preparations as the cellulosic source.

TABLE II

| Dosage | Grams/Liter Ethanol | |
|---|---|---|
| mg protein/ gram cellulose | Cytolase 123 | High β-Glu Prep |
| 10 | 2.1 | 5.0 |
| 20 | 5.3 | 7.2 |
| 30 | 6.9 | 8.8 |
| 40 | 8.0 | 9.3 |
| 50 | 8.5 | 9.3 |
| 60 | 8.5 | 9.3 |

From Table II it can be clearly seen that the enhance β-glucosidase preparation prepared according to the present invention enhances the production of ethanol compared to a cytolase 123 control, especially at the lower protein concentrations.

In yet another embodiment of this invention, the deletion of the bgl1 gene from *T. reesei* strains would be particularly useful in preparing cellulase compositions for use in the detergents and in isolating cellobiose. The cellulase enzymes have been used in a variety of detergent compositions to enzymatically clean clothes. However, it is known in this art that use of cellulase enzymes can impart degradation of the cellulose fibers in clothes. One possibility to decrease the degradation effect is to produce a detergent that does not contain β-glucosidase. Thus, the deletion of this protein would effect the cellulase system to inhibit the other components via accumulation of cellobiose. The modified microorganisms of this invention are particularly suitable for preparing such compositions because the bgl1 gene can be deleted leaving the remaining CBH and EG components resulting in improved cleaning and softening benefits in the composition without degradative effects.

The detergent compositions of this invention may employ besides the cellulase composition (deleted in β-glucosidase), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. For a more thorough discussion, see U.S. application Ser. No. 07/593, 919 entitled "*Trichoderma reesei* Containing Deleted Cellulase Genes and Detergent Compositions Containing Cellulases Derived Therefrom", which is incorporated herein by reference.

In yet another embodiment, the detergent compositions can also contain enhanced levels of β-glucosidase or altered β-glucosidase. In this regard, it really depends upon the type of product one desires to use in detergent compositions to give the appropriate effects.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

Deletion of the bgl1 gene would also provide accumulation of cellobiose in the cellulase system, which can be purified therefrom. In this regard, the present invention presents the possibility to isolate cellobiose from microorganisms in an easy and effective manner.

Moreover, the present invention also contemplates the use of the β-glucosidase nucleotide sequence to design various probes for the identification of the extracellular β-glucosidase gene in other filamentous fungi. In this regard, the entire nucleotide sequence of the bgl1 gene can be used or a portion thereof to identify and clone out the equivalent genes from other filamentous fungi. The sources of filamentous fungi include those fungi from the genus Trichoderma, Aspergillus, Neurospora, Humicola, Penicillium and the like. More particularly, the preferred species include *Trichoderma reesei, Trichoderma viridae, Aspergillus niger, Aspergillus oryzae, Neurospora crassa, Humicola grisea, Penicillium pinophilum, Penicillium oxalicum, Aspergillus phoenicis, Trichoderma koningii* and the like. Due to the species homology of the ba11 gene, filamentous fungi equivalent genes are easily identified and cloned. Indicative of this is FIG. 8, which is an autoradiograph of *A. nidulans* and *N. crassa* genomically DNA digested with Hind III and Eco RI, which further were blotted and probed with a DNA fragment containing the bgl1 gene of *T. reesei*. This autoradiograph clearly illustrates that a DNA fragment containing the bgl1 gene of *T. reesei* can be used to identify this extracellular bgl1 gene in other fungi.

In order to further illustrate the present invention and advantages thereof, the following specific examples are given, it being understood that the same are intended only as illustrative and in nowise limitative.

EXAMPLE 1

Isolation of Total RNA from *Trichoderma reesei*

A *Trichoderma reesei* culture which over produces cellulases was specifically induced for cellulase using sophorose, a β,1–2 diglucoside as described by Gritzali, 1977. The starting strain of *Trichoderma reesei* is a cellulase production strain developed by mutagenesis by the methods described by Sheir-Neiss, G. and Montenecourt, B. S., *Appl. Microbiol. Biotechnol.*, Vol. 20 (1984) pp. 46–53. A mycelial inoculum of *T. reesei*, from growth on potato dextrose agar (Difco), was added into 50 ml of Trichoderma basal medium containing 1.40 grams/liter $(NH_4)_2.SO_4$, 2.0 grams/liter $KH_2PO_4$, 0.30 grams/liter $MgSO_4$, 0.30 grams/liter urea, 7.50 grams/liter BactoPeptone, 5.0 ml/liter, 10% Tween-80, 1.0 ml/liter trace elements-EFG, pH 5.4, which was filtered through a 0.2 micron filter in a 250 ml baffled flask. This culture was incubated at 30° C. for 48 hours with vigorous aeration. Five milliliter aliquots were taken from the culture and added to 25 ml of fresh basal medium in seven 250 ml flasks. These were subsequently grown for 24 hours at 30° C. All cultures were centrifuged in a benchtop clinical centrifuge at 2400×g for 10 minutes. The mycelial pellets were washed three times in 50 mls of 17 mM $KHPO_4$ buffer (pH 6.0). Lastly, the mycelia were suspended in six flasks containing 50 ml of 17 mM $KHPO_4$ buffer with the addition of 1 mM sophorose and a control flask containing no sophorose. The flasks were incubated for 18 hours at 30° C. prior to harvesting by filtration through Mira-cloth (Calbiochem). The excess medium was then squeezed out and the mycelial mat was placed directly into liquid nitrogen and may be stored at −70° C. for up to one month. The frozen hyphae were then ground in an electric coffee grinder that was pre-chilled with a few chips of dry ice until a fine powder was obtained. The powder was then added to about 20 ml of an extraction buffer containing 9.6 grams of p-aminosalicylic acid dissolved in 80 ml of DEP-treated water, 1.6 grams of tri-isopropylnaphthalene sulfonic acid dissolved in 80 ml of DEβ-treated water, 24.2 grams Tris-HCl, 14.6 grams NaCl, 19.09 grams EDTA, which was diluted to 200 ml total volume with DEβ-treated water and the pH adjusted to 8.5 with NaOH. After addition of the extraction buffer, 0.5 volumes of TE-saturated phenol was also added thereto, and the extraction mixture was placed on ice. One quarter volume of chloroform was then added to the extraction mixture, and the mixture was shaken for two minutes. The phases were then separated by centrifugation at 2500 rpm. The aqueous phase was removed and placed in a centrifuge tube, which contained a few drops of phenol in the bottom of said tube. The tube was placed on ice. The organic phase was then reextracted with 2.0 ml of extraction buffer and placed in a 68° C. water bath for 5 minutes to release the RNA trapped in polysomes and at the interface of the extraction mixture. The extracted mixture was then centrifuged, and the aqueous phase removed and pooled with the other aqueous fraction.

The entire aqueous fractions were then extracted with phenol-chloroform (1:1 v/v) for 4 to 5 times until there was no longer any protein seen visually at the interface. Then 0.1 volume of 3 M sodium acetate, pH 5.2 (made with DEP water and autoclaved) and 2.5 volumes of 95% was added to the organic extracts, and the extracts were frozen at −20° C. for 2 to 3 hours. Alternatively, the RNA was precipitated using 2 M lithium acetate. The RNA was then pelleted by centrifugation at 12,000 rpm for 20 minutes. The pelleted RNA was then resuspended in DEβ-water with an RNase inhibitor to a final concentration of 1 unit per μl. To determine whether the genes encoding the enzymes were being induced, total RNA was analyzed.

Analysis of Total RNA Preparation

To confirm whether the genes encoding the enzymes of the cellulase complex were being induced, total RNA was analyzed by Northern blotting as described by Maniatis et al, supra using a fragment of the *T. reesei* cbh2 gene as a probe. The cbh2 clone was isolated using the methods described by Chen et al in "Nucleotide Sequence and Deduced Primary Structure of Cellobiohydrolase II from *Trichoderma reesei*", *Biotechnology*, Vol. 5 (March 1987), incorporated herein by reference. Site directed mutagenesis was performed on the cDNA clone and a Bgl II site was placed at the exact 5' end of the opening reading frame and an Nae I site at the exact 3' end. The Bgl II/Nae I coding sequence was then cloned into a pUC218 phagemid. For use as a probe, the gene was cut out after gel isolation. The results indicated that the level of cbh2 specific mRNA reached a peak at 14–18 hours post induction. The total RNA from 14, 18 and 22 hours was then pooled.

EXAMPLE 2

Purification of Polyadenylated mRNA mRNA was then isolated from the pooled fraction of total RNA set forth above using oligo (dT) cellulose chromatography. Oligo(dT) cellulose (type 3 from Collaborative Research, Lexington, Mass.) is first equilibrated with oligo (dT) binding buffer containing 0.01 M Tris-HCl, pH 7.5, 0.5 M NaCl, and 1 mM EDTA, then aliquots of 25–300 mg were added to 1.5 ml microfuge tubes. RNA dissolved in 1 ml of binding buffer was added and allowed to bind for 15 min. with gentle shaking. The suspensions were centrifuged at 1500 g for 3–5 min., washed 3–5 times with 1 ml of binding buffer, and then washed 3 times with 400 μl of elution buffer containing 0.01 m Tris-HCl, pH 7.5, and 1 mM EDTA. The eluates were pooled, readjusted to 0.5 M NaCl, rebound, and reeluted with three washes of elution buffer. The final three elution buffer washes were pooled and mRNA was recovered by ethanol precipitation.

Analysis of Total RNA and polyadenylated mRNA

Total RNA and the polyadenylated RNA were fractionated on 1% formaldehyde-agarose gels using 10 μg of RNA for each lane, blotted to Nytran® membranes and analyzed by the Northern blot method described by Thomas in "Hybridization of denatured RNA and Small DNA fragments transferred to Nitrocellulose", *Proc. Nat. Acad. Sci. USA*, Vol. 77 (1980), pp. 5201–5205.

Briefly, this procedure involves denaturing RNA (up to 10 μg/8 μl reaction) by incubation in 1 M glyoxal/50% (vol/vol) Me$_2$SO/10 mM sodium phosphate buffer, pH 7.0 at 50° C. for 1 hr. The reaction mixture was cooled on ice and 2 μl of sample buffer containing 50% (vol/vol) glycerol, 10 mM sodium phosphate buffer at 7.0 and bromophenol blue was added. The samples were electrophoresed on horizontal 1% formaldehydeagarose gels in 10 mM phosphate buffer, pH 7.0 at 90 v for 6 hours.

The glyoxylated RNA was transferred from agarose gels to nitrocellulose by using 3 M NaCl/0.3 M trisodium citrate (20× NaCl/cit). After electrophoresis, the gel was placed over two sheets of Whatman 3 MM paper which was saturated with 20× NaCl/Cit. The nitrocellulose paper was wetted with water, equilibrated with 20× NaCl/Cit and laid over the gel. The gel was then covered with two sheets of Whatman 3 MM paper and a 5 to 7 cm layer of paper towels, a glass plate and a weight. Transfer of the RNA was completed in 12–15 hours. The blots were then dried under a lamp and baked in a vacuum for over 2 hrs. at 80° C.

The membranes were probed with a cbh2 probe to verify that the polyadenylated mRNA pool contained cbh2 mRNA and by inference the genes encoding the enzymes of the cellulase complex were indeed induced.

EXAMPLE 3

Synthesis of CDNA

A. First Strand Synthesis

Synthesis of CDNA was performed using the BRL CDNA Synthesis System® (Bethesda Research Laboratories, Md.) according to the instructions of the manufacturer. To a sterile, DEPC-treated tube in ice was added 5× First Strand Buffer containing 250 mM Tris-HCl, pH 8.3, 2.5 μl 10 mM dNTP Mix (10 mM DATP, 10 mM dCTP, 10 mM dGTP, 10 mM dTTP), 5 μl Oligo (dT)$_{12-18}$ (0.5) mg/ml), 10 μl of mRNA and 20 μl of mRNA and 20 μl DEPC-treated water to create a final composition containing 50 mM Tris-HCl (pH 8.3), 75 mM KCl, 3 mM MgCl$_2$, 10 mM dithiothreitol, 500 μM each dATP, dCTP, dGTP and dTTP, 50 μg/ml Oligo (dT)$_{12-18}$, 100 μg/ml polyadenylated RNA and 10,000 U/ml cloned M-MLV Reverse Transcriptase. A control run was also run simultaneously using 10 μl of a 2.3 kb control RNA (0.5 mg/ml) in lieu of the mRNA.

The reaction was initiated by adding 2.5 μl of M-MLV reverse transcriptase (200 μ/μl) to the mRNA tube and the control RNA. The samples were mixed. All reaction tubes were incubated at 37° C. for one hour and then placed on ice.

A small aliquot from the reaction mixture was run on a gel to confirm its presence and quantity. The yield obtained was about 2–6 μg.

B. Second Strand Synthesis

To the control tube on ice after first strand synthesis was added 230.6 μl DEPC-treated water, 6 μl 10 mM dNTP mix, 32 μl 10× second strand buffer containing 188 mM Tris-HCl, pH 8.3, 906 mM KCl, 100 mM (NH$_4$)$_2$ SO$_4$, 46 mM MgCl$_2$, 37.5 mM dithiothreitol, 1.5 mM NAD, 8 μl E. coli DNA Polymerase I (10 μ/μl), 1.4 μl E. coli RNase 4 and 1 μl E. coli DNA ligase (100 units).

To the first strand synthesis of the sample was added on ice 289.5 μl of DEPC-treated water, 7.5 μl 10 mM dNTP mix, 40 μl 10× second strand buffer, 10 μl E. coli DNA Polymerase I, 1.75 μl E. coli RNaseH and 1.25 E. coli DNA ligase, to create a final composition containing 25 mM Tris-HCl (pH 8.3), 100 mM KCl, 10 mM (NH$_4$)$_2$SO$_4$, 5 mM MgCl$_2$, 250 μM each DATP, dCTP, dGTP, dTTP, 0.15 mM NAD, 5 mM Dithiothreitol, 250 U/ml DNA Polymerase I, 8.5 U/ml RNase H, and 30 U/ml DNA Ligase. Both the control tube and the sample tube were vortexed gently and incubated for 2 hours at 16° C. After incubation, both tubes were placed on ice.

The sample tube was then extracted with 415 μl of phenol and ethanol precipitated. The pellet was dissolved in 200 μl of sterile TE buffer (10 mM Tris-HCl pH 7.5, 1 mM Na$_2$EDTA) and reprecipitated from 7.5 M ammonium acetate with ethanol.

An aliquot of the sample was further analyzed by gel electrophoresis to check for purity. The yield of the synthesis was about 4.0 μg.

The remaining control sample was further extracted with phenol and ethanol precipitated as described above for the sample. After dissolving the pellet in 200 μl of sterile TE buffer, reprecipitating the sample from ammonium acetate with ethanol, and redissolving the dry pellet in 20 μl of sterile TE buffer, 2 μl of the solution was then further analyzed by gel electrophoresis to check for purity.

EXAMPLE 4

Amplification of bgl1 CDNA Sequences

Amplification of the cDNA fragments encoding a portion of the T. reesei β-glucosidase gene, bgl1, was performed using the polymerase chain reaction (PCR) method with Taq® polymerase and a Perkin Elmer Cetus Thermal Cycle®.

The reaction mixture was formed by mixing 76 μl deionized water, 10 μl of a 10× mixture of buffer containing 166 mM (NH$_4$)$_2$ SO$_4$, 670 MM Tris-HCl, pH 8.8, 67 mM MgCl$_2$, 67 μm EDTA, 10 mM β-mercaptoethanol, 10 μl dimethylsulfoxide and 1.7 mg/ml BSA diluted to a total volume of 1.0 ml with deionized water, 8 μl of 2 dNTPs (each), 1 μl 5' mer oligonucleotide primer, 1 μl 3' mer oligonucleotide primer, 1.0 μg cDNA diluted in 3 μl deionized water, and 1 μg Taq® polymerase.

The amplification method consists of an initial denaturing cycle at 95° C. for 10 minutes, followed by a two minute annealing step at 50° C. and a 10 minute polymerization cycle at 65° C., for an additional 30 cycles.

A. Oligonucleotide Primers

The oligonucleotide primers used to amplify the cDNA fragment encoding the T. reesei bgl1 gene were designed based on the degeneracy of the genetic code for the selected amino acids for an N terminal region of the bgl1 gene and an internal oligonucleotide. The N. terminal oligonucleotide primer consisted of the sequence (SEQ ID NO: 3):

5' GCI GTI GTI CCT CCT GCI GG wherein I=inosine.

The internal oligonucleotide primer consisted of a pool of 16×21 mers. This pool was based on various derivations of the following sequences (SEQ ID NO: 4):

5' GTT G/ATT ICC G/ATT G/AAA G/ATC TGT

EXAMPLE 5

Subcloning of PCR Generated Fragments

Ninety μl of each reaction mix was fractionated on 4% polyacrylamide gels in 1× TBE, the major band was excised and eluted from the gel slice as described by Maniatis et al (1982), supra. The eluted DNA fragment was precipitated in ethanol and resuspended in 15 μl of 10 mM Tris, 1 mM EDTA (TE). Each 1–2 μg DNA fragment was then treated with 0.5 mM ATP and R$_4$ polynucleotide kinase to phosphorylate the 5' end of each fragment followed by the procedures of Maniatis et al. Blunt ends were generated by adding 3 μl of 10× T$_4$ polymerase buffer (330 mM Tris-acetate at pH 7.9, 660 mM potassium acetate, 100 mM magnesium acetate, 1 μl of 2.5 mM dNTPs, 1 μl of T$_4$ DNA polymerase and 5 μl of distilled water. The blunt-end reaction mixture was then incubated at 37° for 60 minutes. The reaction was stopped by addition of EDTA to a final concentration of 1 mM EDTA and the sample was further heated for 10 minutes at 65° C.

The blunt-end DNA fragments were then ligated with SmaI cleaved and dephosphorylated pUC218 which had been infected with M13X07 as described by Maniatis et al, supra.

The cloning vectors pUC218 and pUC219 were derived from pUC118 and pUC119 by insertion of the Bgl II, Cla I and Xho I polylinker as described by Korman et al in "Cloning, Characterization, and expression of two α-amylase genes from Aspergillus niger var. awamori", Current Genetics, Vol. 17, pp. 203–212 (1990).

The aforedescribed phagemid was then used to transform E. coli strain JM101 as described by Yarnisch et al in "Improved M13 phage cloning vectors and host strains: nucleotide sequence of the M13 MP18 and pUC19 Vectors", Gene, Vol. 1197, pp. 103–119 (1985).

EXAMPLE 6

Isolation of cDNA Subcloned Fragment

The transformed strain was inoculated in 1.5 ml of 2YT broth in a tube which had been previously inoculated with 15 μl of saturated E. coli JM101. The culture was grown for 8 hours under shaking at 37° C.

The culture mixture was then spun at 6000 rpm for 5 minutes, and the supernatant was poured off into another tube. To the supernatant 300 μl of 2.5 M NaCl, 20% PEG was added, and the solution was mixed. The mixture was then incubated at room temperature for 15 minutes.

The solution was then spun for 5 minutes in a microfuge, and the supernatant was aspirated off. The solution was vortexed once again, and the supernatant was further aspirated off.

100 μl of equilibrated phenol was added to the tube, and the tube was vortexed. 100 μl of chloroform was added, and once again the tube was vortexed. The tube was heated at 55° C. for 5 minutes, mixed, and microfuged an additional 5 minutes.

160 μl of the supernatant was then pipetted off and transferred to a clear tube. 20 μl of 1N NaOAC, pH 4.5, 400 μl of 95% ETOH was added to the supernatant, and the solution was mixed and frozen on dry ice for 5 minutes. The tube was then spun for an additional 15 minutes, and the supernatant was aspirated off.

1000 μl of 70% Ethanol was added to the tube, and the tube was spun for an additional 2 minutes and reaspirated. The mixture was spun once more under vacuum for 4 minutes, and the pellet was resuspended in 15 μl TE buffer.

Determination of the Nucleotide Sequence of 700 bp cDNA fragment

The nucleotide sequence of the 700 bp cDNA fragment was determined using the dideoxy DNA sequencing method described by Sanger et al, "DNA Sequencing with chain terminating inhibitors", *Proc. Nat. Acad. Sci. U.S.A.,* Vol. 74 (1977), p. 5463, using the Sequenase® reagent kit (U.S. Biochemicals).

Identification of bgl1 gene from *T. reesei*

The 700 bp bgl1 cDNA fragment was then labelled with $^{32}$P using methods described by Maniatis et al, supra.

Genomic DNA from *T. reesei* was prepared by filtering a 24–36 hour culture of *T. reesei* through Miracloth and freezing the mycelia obtained from the culture medium. The frozen mycelia were then ground into a fine powder and 22 mls of TE, and 4 mls of 20% SDS were added to the powdered mycelia and mixed. 10 mls of phenol and chloroform was added to the mixture prior to centrifugation and removal of the aqueous phase. 200 μl of 5 mg/ml proteinase K was added to the organic extract, and the mixture was incubated for 20 minutes at 55° C. The DNA was then further extracted by methods known in the art using chloroform/phenol extraction followed by ethanol precipitation. The isolated DNA was then treated with 1 μg of heated ribonuclease A (100° C. for 15 minutes) per 20 μg of genomic DNA in TE buffer at 37° C. for 30 minutes, then cooled to room temperature. The genomic DNA from *T. reesei* was then cut with a variety of restriction enzymes such as Eco RI, Hind III and the like, Southern blotted and hybridized with the 700 bp cDNA fragment of the bgl1 gene as a probe. From this analysis it was determined that Hind III was the restriction enzyme of choice used to locate a 6 kb fragment.

10 to 20 Units of Hind III per milligram of genomic DNA was added to the treated DNA and then the DNA was extracted with phenol-chloroform to remove protein, alcohol precipitation and the DNA was resuspended to 2 grams/liter in TE buffer.

4 μl samples from the Hind III digestion of genomic DNA were loaded on a 1% agarose gel and fractionated electrophoretically. The gel was then Southern blotted and probed with the 700 bp cDNA probe. A 6.0 kb band was identified on the Southern blot of Hind III digested genomic DNA from *T. reesei*.

The remaining Hind III genomic DNA was then subjected to a preparative electrophoresis and fragments ranging from 5 kb to 7 kb were then electroeluted from the agarose gel and cloned into pUC218 and transformed with *E. coli* JM181 to create a library. Then the library was screened by colony hybridization using 700 bp bgl1 cDNA as a probe.

The positive colonies from the transformation were then picked and the DNA isolated therefrom by phenol:chloroform extraction and ethanol precipitation, described by Maniatis et al, supra.

The isolated DNA from the positives were digested both singly and in various combinations with the following restriction enzymes: Hind III, Eco RI, Sst 1, Kpn I, Bam HI, Xho 1, Bgl II, Cla I, Xba I, Sal I, Pst I, Sph I, Bal I, and Pvu II. The digestions were subjected to agarose gel electrophoresis, and the resultant banding pattern was used to contruct a restriction map of the cloned 6.0 kb genomic DNA. The same agarose gel was Southern blotted and probed with the 700 bp bgl1 cDNA to identify which genomic restriction fragments shared homology with the bgl1 cDNA. The mapping experiments confirmed that the entire bgl1 gene is contained on the genomic Hind III clone. Pvu II and Bal I restriction fragments which ranged in size from 600 bp to 1500 bp hybridized with the 700 bp DNA bgl1 clone and were chosen for subcloning into pUC218 phagemid. After cloning these fragments into the phagemid, the Pvu II and Bal I subclones were then sequenced using the dideoxy chain termination method of Sanger et al (1977). It was then determined from this sequencing that the overlapping sequences of the subclones aligned with a single contiguous sequence totaling 3033 bp within which the nucleotide sequence was determined on both strands.

Analysis of bgl1 gene

A. Sequence Analysis

Nucleotide sequencing was done by the dideoxy chain termination method of Sanger et al (1977) using the Sequenase® reagent kit (U.S. Biochemicals).

B. Amino Acid Sequencing

A 2.5-nmol sample of the reduced and carboxymethylated β-glucosidase preparation was subjected to N-terminal sequencing on a proprietary multiphase sequencer.

To a sample of β-glucosidase, Endo-Lys C protease was added to 1% of the total protein and the mixture incubated for 1 hour at 37° C. or the protein sample was subject to cyanogen bromide treatment. An equal volume of HPLC solution A (0.05% TEA/0.05% TFA in water) was added to stop the reaction. The resulting CNBr and Endo-Lys C fragments were separated by chromatography on a Brownlee C-4 column using a linear gradient of 0–100% HPLC solution B (0.05% TEA/0.05% TFA in n-propanol) at a rate of 1% per minute. Several peaks were collected for amino acid sequencing and the data are denoted in FIG. 1.

Construction of pSASβ-glu

The starting vector for the construction of pSASβ-glu was the plasmid pSAS. pSAS was constructed in the following way. pUC100 (a commercially available plasmid vector) was digested with the restriction enzyme SmaI and the 5' phosphate groups subsequently removed by digestion with Calf alkaline phosphatase. The linear vector fragment was purified from undigested vector and protein by agarose gel electrophoresis followed by isolation of the vector DNA from the isolated gel slice by electroelution. The amds gene was isolated as a 2.4 Kb SstI restriction fragment following separation from the vector sequences (contained in—Hynes, M. J., Corrick, C. M., and King, J. A., "Isolation of genomic clones containing the amds gene of *Aspergillus nidulans* and their use in the analysis of structural and regulatory mutations", *Mol. Cell. Biol.,* Vol. 3 (1983), pp. 1430–1439).

The 2.4 kb SstI amdS fragment and the 2.7 kb pUC10 vector fragment were then ligated together and the ligation mix transformed and propagated in the E. coli host strain, JM101.

pSASβ-glu was constructed by digesting PSAS with the restriction enzyme Hind III, and purifying the linear fragment as described above. Into this Hind III treated pSAS vector fragment was ligated a 6.0 kb Hind III fragment of T. reesei genomic DNA that contained all of the coding region of the bgl1 gene along with sequences necessary for the genes transcription and translation.

EXAMPLE 7

Isolation of Protoplasts

Mycelium was obtained by inoculating 100 ml of YEG (0.5% yeast extract, 2% glucose) in a 500 ml flask with about $5 \times 10^7$ T. reesei (the amds mutant strain). The flask was then incubated at 37° C. with shaking for about 16 hours. The mycelium was harvested by centrifugation at 2,750×g. The harvested mycelium were further washed in 1.2 M sorbitol solution and resuspended in 40 ml of Novozym®, which is the tradename for a multicomponent enzyme system containing 1,3-alpha-glucanase, 1,3-beta-glucanase, laminarinase, xylanase, chitinase and protease from Novo Biolabs, Danbury, Conn., solution containing 5 mg/ml Novozym® 234; 5 mg/ml $MgSO_4.7H_2O$; 0.5 mg/ml bovine serum albumin; 1.2 M sorbitol. The protoplasts were removed from cellular debris by filtration through Miracloth (Calbiochem Corp.) and collected by centrifugation at 2,000×g. The protoplasts were washed three times in 1.2 M sorbitol and once in 1.2 M sorbitol, 50 mM $CaCl_2$, centrifuged and resuspended. The protoplasts were finally resuspended at a density of $2 \times 10^8$ protoplasts per ml of 1.2 M sorbitol, 50 mM $CaCl_2$.

EXAMPLE 8

Transformation of Fungal Protoplasts

200 μl of the protoplast suspension prepared in Example 2 was added to 20 μl (20 μg) of pSASβ-glu in TE buffer (10 mM Tris, pH 7.4; 1 mM EDTA) and 50 μl of a polyethylene glycol (PEG) solution containing 25% PEG 4000, 0.6 M KCl and 50 mM $CaCl_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2 M sorbitol and 50 mM $CaCl_2$ was added thereto and this solution was further mixed. The protoplast solution was then immediately added to molten aliquot's of Vogels Medium N (3 grams sodium citrate, 5 grams $KH_2PO_4$, 2 grams $NH_4NO_3$, 0.2 grams $MgSO_4.7H_2O$, 0.1 gram $CaCl_2.2H_2O$, 5 μg α-biotin, 5 mg citric acid, 5 mg $ZnSo_4.7H_2O$, 1 mg $Fe(NH_4)_2.6H_2O$, 0.25 mg $CuSO_4.5H_2O$, 50 μg $MnSO_4.4H$ containing an additional 1% glucose, 1.2 M sorbitol and 1% agarose. The protoplast/medium mixture was then poured onto a solid medium containing the same Vogel medium as stated above containing in addition acetamide as a nitrogen source. Since T. reesei does not contain a functional equivalent to the amdS gene only transformants will grow on this medium. These colonies were subsequently transferred and purified on a solid Vogel's medium N containing as an additive, 1% glucose. The bgl1 gene inserted transformant strain is called A83pSASβGlu.

FIG. 4 is an autoradiograph of a Southern blot using the 700 bp fragment as a probe, of the different transformants with enhanced copies of the bgl1 gene using genomic T. reesei from an overproducing strain digested with Hind III as a control. This autoradiograph clearly shows that the transformants contained enhanced amount of the bgl1 gene compared with the control.

FIG. 3 is a Northern blot of RNA isolated from one of the transformed strains produced by the present invention following induction with soporose illustrating a corresponding increase in the levels of bgl1 message when compared to the parental strain of T. reesei.

Besides visual analysis of the transformants, quantitative analysis was also completed by cutting the appropriate bands out of the Nytran® membrane and counting the radioactive label present therein in a scintillation counter. This experiment was performed to obtain a more precise estimate of the relative amounts of message as shown in Table III below:

TABLE III

| CPM | Parental Trichoderma reesei strain | Transformed Trichoderma reesei strain |
|---|---|---|
| CPM β-glu message | 14.4 | 25.4 |
| CPM CBHII | 227.1 | 95.2 |
| CPM β-glu/ CBHII | 0.0634 | 0.2668 |

Table III illustrates that the transformant produced by the process of the present invention has extra β-glucosidase mRNA and hence an increase in β-glucosidase enzyme resulting in an increase in specific activity.

While the invention has been described in terms of various preferred embodiments, the skilled artisan will appreciate that various modifications, substitutions, omissions, and changes may be made without departing from the scope thereof. Accordingly, it is intended that the scope of the present invention be limited solely by the scope of the following claims, including equivalents thereof.

What is claimed is:

1. A process for expressing extracellular β-glucosidase from DNA encoding an extracellular β-glucoidase which DNA is obtained from a microorganism selected from the group consisting of Trichoderma, Aspergillus, and Neurospora, and wherein said DNA sequence or a portion thereof is capable of amplification by PCR with SEQ ID NO: 3 and SEQ ID NO: 4, wherein the amplification conditions are denaturation at 95° C. for 10 minutes, annealing at 50° C. for 2 minutes and extension at 65° C. for 10 minutes for 30 cycles and wherein the amplification product is a DNA sequence that comprises a DNA sequence of about 700 base pairs from about position 471 to about position 1171 of SEQ ID NO: 1, comprising:

expressing said extracellular β-glucosidase from a DNA insert through recombinant techniques in a filamentous fungus, wherein the inserted DNA comprises all of the coding region of a fungal β-glucosidase gene and sequence necessary for the β-glucosidase gene's transcription and translation, and wherein said filamentous fungus is selected from the group consisting of Trichoderma, Aspergillus, Neurospora, Humicola and Penicillium.

2. The process according to claim 1, further comprising the step of isolating transformants having at least one additional copy of a fungal gene encoding for extracellular β-glucosidase.

3. The process according to claim 2, further comprising the steps of: (a) culturing said transformants under conditions to permit growth of said transformants; and (b) isolating a recombinant fungal cellulase composition produced from said transformant.

4. The process according to claims 3, further comprising the step of purifying the β-glucosidase from said isolated recombinant fungal cellulase composition.

5. The process according to claim 1, wherein said filamentous fungus is *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisea, Penicillium pinophilum,* or *Penicillium oxalicum.*

6. The process according to claim 1 wherein said β-glucosidase gene is a bgl1 gene derived from *Trichoderma reesei.*

7. The process according to claim 3, wherein said recombinant fungal cellulase composition is isolated by:
(a) centrifuging said culture medium containing said transformants having β-glucosidase activity to form a supernatant and a pellet; and
(b) filtering said supernatant to obtain a recombinant fungal cellulase composition.

8. The process according to claim 7, wherein an antimicrobial agent is added to said recombinant fungal cellulase composition after filtration.

9. The process according to claim 6, wherein said deleted bgl1 gene comprises the amino acid sequence and nucleotide sequence from base nos. 311 to 2679 of SEQ ID NO: 1.

10. Transformants having at least one additional copy of a *T. reesii* fungal gene encoding for extracellular β-glucosidase produced by the process according to claim 2.

11. A process for expressing extracellular β-glucosidase, comprising a) inserting DNA encoding an extracellular β-glucosidase gene obtained from a microorganism selected from the group consisting of Trichoderma, Aspergillus, and Neurospora, wherein said DNA sequence or a portion thereof is capable of amplification by PCR with SEQ ID NO: 3 and SEQ ID NO: 4, wherein the amplification conditions are denaturation at 95° C. for 10 minutes, annealing at 50° C. for 2 minutes and extension at 65° C. for 10 minutes for 30 cycles and wherein the amplification product is a DNA sequence that comprises a DNA sequence of about 700 base pairs from about position 471 to about position 1171 of SEQ ID NO: 1, and wherein said host fungus is selected from the group consisting of Trichoderma, Aspergillus, Neurospora, Humicola and Penicillium; b) isolating transformants having enhanced β-glucosidase expression as compared to a nontransformed filamentous host; c) culturing said transformants under conditions to permit growth of said transformants; and d) isolating a fungal cellulase composition containing the β-glucosidase from said transformants.

12. The process according to claim 11 wherein the extracellular β-glucosidase gene is a bgl1 gene having the nucleotide sequence of SEQ ID NO: 1.

13. The process according to claim 11 wherein the extracellular β-glucosidase gene encodes a polypeptide comprising the amino acid sequence of SEQ ID NO: 2.

14. The process according to claim 11 wherein said host fungus is a transformed Trichoderma.

15. A probe for use in detecting nucleic acid sequences encoding β-glucosidase from a filamentous fungi comprising SEQ ID. NO: 1.

16. The probe of claim 15 wherein said probe is used to detect a nucleic acid sequence encoding a β-glucosidase from a filamentous fungi selected from the group consisting of Trichoderma, Aspergillus, and Neurospora.

17. A polynucleotide sequence comprising the nucleic acid sequence of SEQ ID NO: 1.

18. An expression vector comprising the polynucleotide of claim 17.

19. A filamentous fungal host transformed with the polynucleotide of claim 17 wherein said host is selected from the group consisting of Trichoderma, Aspergillus, Neurospora, Humicola and Penicillium.

* * * * *